(12) United States Patent
Murata et al.

(10) Patent No.: US 11,282,201 B2
(45) Date of Patent: Mar. 22, 2022

(54) INFORMATION PROCESSING DEVICE, INFORMATION PROCESSING METHOD AND INFORMATION PROCESSING SYSTEM

(71) Applicant: SONY CORPORATION, Tokyo (JP)

(72) Inventors: Rei Murata, Kanagawa (JP); Shinji Watanabe, Tokyo (JP)

(73) Assignee: SONY CORPORATION, Tokyo (JP)

( * ) Notice: Subject to any disclaimer, the term of this patent is extended or adjusted under 35 U.S.C. 154(b) by 369 days.

(21) Appl. No.: 16/332,632

(22) PCT Filed: Oct. 18, 2017

(86) PCT No.: PCT/JP2017/037683
§ 371 (c)(1),
(2) Date: Mar. 12, 2019

(87) PCT Pub. No.: WO2018/083984
PCT Pub. Date: May 11, 2018

(65) Prior Publication Data
US 2021/0287373 A1   Sep. 16, 2021

(30) Foreign Application Priority Data

Nov. 2, 2016 (JP) .............................. JP2016-215195
Sep. 26, 2017 (JP) .............................. JP2017-184807

(51) Int. Cl.
*G06K 9/00* (2006.01)
*G06T 7/00* (2017.01)
(Continued)

(52) U.S. Cl.
CPC ........ *G06T 7/0016* (2013.01); *G06K 9/00147* (2013.01); *G06K 9/3233* (2013.01);
(Continued)

(58) Field of Classification Search
None
See application file for complete search history.

(56) References Cited

U.S. PATENT DOCUMENTS

| 2015/0213302 A1* | 7/2015 | Madabhushi ...... G06K 9/00147 |
| | | 382/133 |
| 2016/0073020 A1 | 3/2016 | Matsumoto |
| 2017/0073630 A1 | 3/2017 | Matsubara |

FOREIGN PATENT DOCUMENTS

| CN | 105190694 A | 12/2015 |
| EP | 2998934 A1 | 3/2016 |

(Continued)

OTHER PUBLICATIONS

Huh, et al., "Detection of Mitosis within a Stem Cell Population of High Cell Confluence in Phase-Contrast Microscopy Images", Conference on Computer Vision and Pattern Recognition (CVPR), IEEE, Aug. 22, 2011, pp. 1033-1040.

(Continued)

*Primary Examiner* — Soo Jin Park
(74) *Attorney, Agent, or Firm* — Chip Law Group

(57) ABSTRACT

Provided is an information processing device that includes a first information acquisition section that acquires first information on the basis of a still image in a frame corresponding to a predetermined time point, from among a plurality of images of a biological sample captured in a time-series manner, a second information acquisition section that acquires second information on the basis of an interframe change of the plurality of images in a predetermined period, and a determination section that determines an event regarding the biological sample, using the first information and the second information.

15 Claims, 25 Drawing Sheets

(51) Int. Cl.
*G06K 9/32* (2006.01)
*G06N 3/08* (2006.01)
*G06T 7/20* (2017.01)

(52) U.S. Cl.
CPC ............... *G06N 3/08* (2013.01); *G06T 7/20* (2013.01); *G06T 2207/10056* (2013.01); *G06T 2207/30044* (2013.01)

(56) References Cited

FOREIGN PATENT DOCUMENTS

| EP | 3150693 A1 | 4/2017 |
|---|---|---|
| JP | 2013-085546 A | 5/2013 |
| JP | 2013-198503 A | 10/2013 |
| JP | 2016-509845 A | 4/2016 |
| WO | 2014/185169 A1 | 11/2014 |
| WO | 2015/182381 A1 | 12/2015 |
| WO | 2016/162945 A1 | 10/2016 |
| WO | 2017/169397 A1 | 10/2017 |

OTHER PUBLICATIONS

Huh, et al., "Automated Mitosis Detection of Stem Cell Populations in Phase-Contrast Microscopy Images", Transactions on Medical Imaging, IEEE, vol. 30, No. 3, Mar. 2011, pp. 586-596.
Extended European Search Report of EP Application No. 17867803.3, dated Sep. 20, 2019, 11 pages.
International Search Report and Written Opinion of PCT Application No. PCT/JP2017/037683, dated Jan. 23, 2018, 08 pages of ISRWO.

\* cited by examiner

FIG. 24
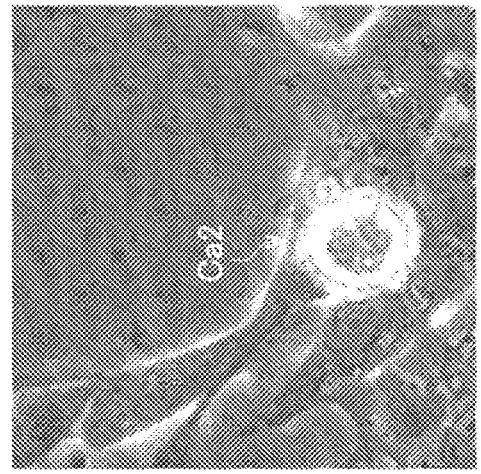
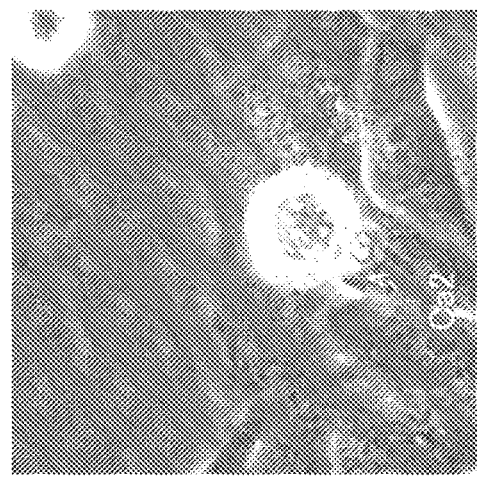
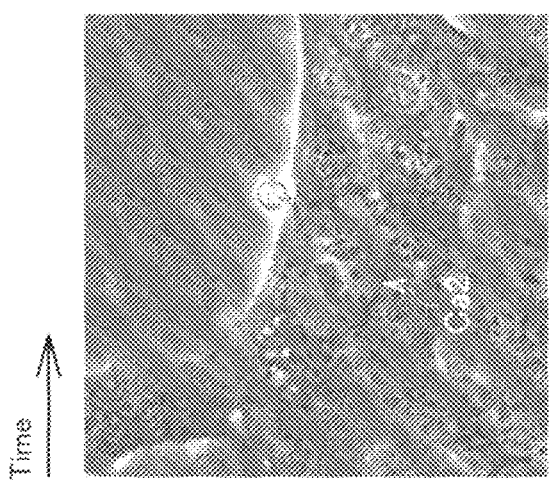

INFORMATION PROCESSING DEVICE, INFORMATION PROCESSING METHOD AND INFORMATION PROCESSING SYSTEM

CROSS REFERENCE TO RELATED APPLICATIONS

This application is a U.S. National Phase of International Patent Application No. PCT/JP2017/037683 filed on Oct. 18, 2017, which claims priority benefit of Japanese Patent Application No. JP 2016-215195 filed in the Japan Patent Office on Nov. 2, 2016 and also claims priority benefit of Japanese Patent Application No. JP 2017-184807 filed in the Japan Patent Office on Sep. 26, 2017. Each of the above-referenced applications is hereby incorporated herein by reference in its entirety.

TECHNICAL FIELD

The present disclosure relates to an information processing device, an information processing method and an information processing system.

BACKGROUND ART

Motion or change of state of a variety of cells and biotissues have been observed in the fields of medical care and life science. Aiming at objectively evaluating these events, development of technologies for determining events regarding the biotissue (for example, cleavages occurring at boundaries between cell stages, morphological changes such as cell division, or degeneration) are underway.

For example, Patent Literature 1 listed below discloses a technique by which a plurality of classifiers is applied to time-series images of embryo to determine classification probability of the embryo, and the embryo is ranked on the basis of such classification probability. Meanwhile, Patent Literature 2 listed below discloses a technique by which the temporal length of cell division stage is measured using time-lapse images (time-series images captured at long intervals such as 30 minutes), and a quality index of embryo is obtained on the basis of the temporal length of cell division stage.

CITATION LIST

Patent Literature

Patent Literature 1: JP 2016-509845T
Patent Literature 2: JP 2013-198503A

DISCLOSURE OF INVENTION

Technical Problem

Both of the aforementioned Patent Literature 1 and Patent Literature 2 are designed to determine an event regarding a biological sample, such as cleavage, by analyzing still images captured at long intervals. It may, however, be difficult in some cases to determine what kind of event is occurring from the captured still images of the biological sample, depending on orientation of the biological sample, features and time of morphological changes in such biological sample, and types of the biological sample.

According to the present disclosure, there is provided a novel and improved information processing device, an information processing method and an information processing system, all capable of determining an event regarding a biological sample in a highly precise manner.

Solution to Problem

According to the present disclosure, there is provided an information processing device including: a first information acquisition section that acquires first information on the basis of a still image in a frame corresponding to a predetermined time point, from among a plurality of images of a biological sample captured in a time-series manner; a second information acquisition section that acquires second information on the basis of an interframe change of the plurality of images in a predetermined period; and a determination section that determines an event regarding the biological sample, using the first information and the second information.

In addition, according to the present disclosure, there is provided an information processing method including, by a processor: acquiring first information on the basis of a still image in a frame corresponding to a predetermined time point, from among a plurality of images of a biological sample captured in a time-series manner; acquiring second information on the basis of an interframe change of the plurality of images in a predetermined period; and determining an event regarding the biological sample, using the first information and the second information.

In addition, according to the present disclosure, there is provided an information processing system including: an imaging device including an imaging unit that produces an image by image capturing; and an information processing device including a first information acquisition section that acquires first information on the basis of a still image in a frame corresponding to a predetermined time point, from among a plurality of images of a biological sample captured by the imaging unit in a time-series manner, a second information acquisition section that acquires second information on the basis of an interframe change of the plurality of images in a predetermined period, and a determination section that determines an event regarding the biological sample, using the first information and the second information.

Advantageous Effects of Invention

As described above, the present disclosure makes it possible to more precisely determine an event regarding a biological sample.

Note that the effects described above are not necessarily limitative. With or in the place of the above effects, there may be achieved any one of the effects described in this specification or other effects that may be grasped from this specification.

BRIEF DESCRIPTION OF DRAWINGS

FIG. 24 contains time-lapse images capturing morphological changes in a single dead cancer cell (group 2), according to the embodiment.

MODE(S) FOR CARRYING OUT THE INVENTION

Figure 1:
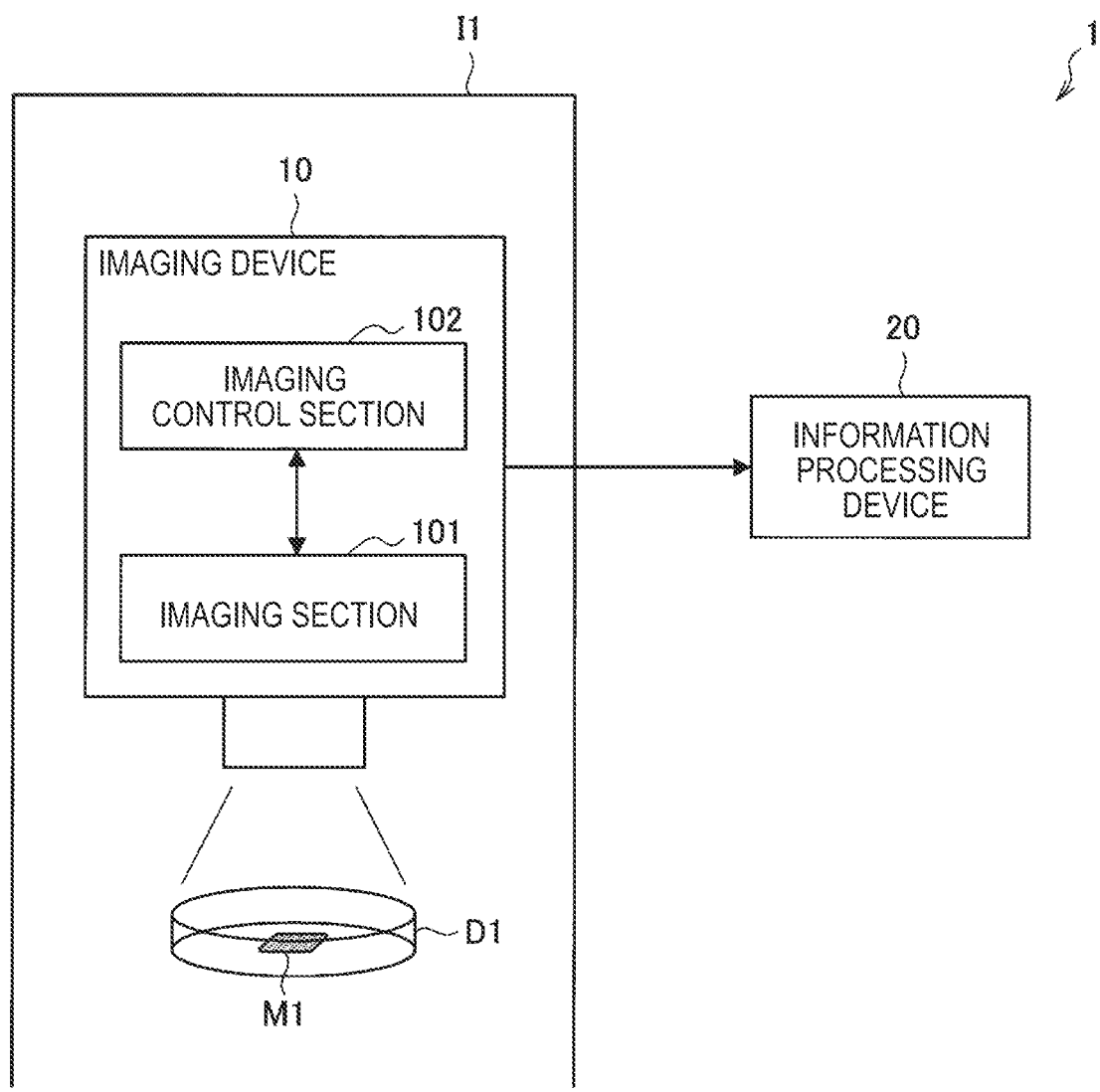
FIG. 1 is a diagram illustrating an overview of a configuration of an information processing system according to an embodiment of the present disclosure.

Hereinafter, (a) preferred embodiment(s) of the present disclosure will be described in detail with reference to the appended drawings. Note that, in this specification and the appended drawings, structural elements that have substantially the same function and structure are denoted with the same reference numerals, and repeated explanation of these structural elements is omitted.

Now, the description will be made following the order below.
1. Overview of Information Processing System
2. First Embodiment
   2.1. Exemplary Configuration
   2.2. Exemplary Processing
3. Second embodiment
   3.1. Exemplary Configuration
   3.2. Exemplary Processing
4. Third embodiment
   4.1. Exemplary Configuration
   4.2. Exemplary Processing
5. Fourth embodiment
6. Exemplary Hardware Configuration
7. Conclusion 1. Overview of Information Processing System FIG. 1 is a diagram illustrating an overview of a configuration of an information processing system 1 according to an embodiment of the present disclosure. As illustrated in FIG. 1, the information processing system 1 has an imaging device 10, and an information processing device 20. The imaging device 10 and the information processing device 20 are connected through a variety of wired or wireless networks.

Imaging Device

The imaging device 10 is a device that produces images (or video) by image capturing. The imaging device 10 according to the embodiment is typically embodied by a digital camera. The imaging device 10 may alternatively be embodied by any of devices with imaging function, such as smartphone, tablet, game machine or wearable device.

The imaging device 10 according to the embodiment is provided, as illustrated in FIG. 1, inside a culture incubator I1, above a dish D1 that contains a medium M1 in which embryo to be observed is cultured. The imaging device 10 captures images of the embryo cultured in the medium M1 at a predetermined frame rate, to thereby produce images.

Now, in a case where a plurality of embryos is present in the dish D1, the embryos may be captured so as to be contained one by one in imaging frames, or may be captured so that a plurality of embryos is contained in a single imaging frame. On the other hand, in a case where a plurality of embryos is individually cultured in a plurality of dishes, it is also possible to capture images of each embryo, while suitably moving the imaging device 10 or the dishes using a freely selectable driving unit provided to the incubator I1.

Now, the imaging device 10 may be provided inside the incubator I1, or outside the incubator I1. Alternatively, the imaging device 10 is applicable to image capturing of embryos which are not housed in the incubator I1. Still alternatively, the imaging device 10 may be provided integrally with the incubator I1.

In addition, the incubator I1 is not specifically limited in terms of specification or size, thus allowing use of any incubator which is capable of providing an environment suitable for culturing embryo. Also regarding the dish D1 and the medium M1, those known to be suitable for culturing embryo are employable.

In more details, the imaging device 10 according to the embodiment has an imaging section 101 and an imaging control section 102, as illustrated in FIG. 1.

The imaging section 101 has various components including an image sensor such as CCD (Charge Coupled Device) or CMOS (Complementary Metal Oxide Semiconductor), a lens that controls focusing of an object image on the image sensor, and a light source that illuminates an object, and captures images of real space using these components.

In order to correctly specify motion inside the embryo to be observed, the imaging section 101 according to the embodiment captures images of a predetermined imaging region that contains embryo(s) cultured on the medium M1. The imaging section 101 may capture images of embryo directly (without being interposed by other component, such as lens), or may capture images of embryo while being interposed by other component such as a microscope with an objective lens. In this design, the objective lens preferably has a magnification of 40× to 60× or around, for the purpose of capturing motion of embryo in sub-micron order. While the frame rate is not specifically limited, it is preferably preset depending on the extent of changes of a target to be observed. More specifically, the frame rate is preferably preset to a value so that motion of embryo in sub-second order may be captured.

The imaging section 101 may be provided with a plurality of imaging modules. More specifically, the imaging device 10 may be provided with an imaging module for time-lapse capturing and an imaging module for video shooting described later. With such design, it now becomes possible to produce images that satisfy performances, including picture quality, individually required for the time-lapse images and video.

A signal generated as a result of image capturing by the imaging section 101 is output to the imaging control section 102.

The imaging control section 102 has a processing circuit built up with a CPU (Central Processing Unit), ROM (Read Only Memory), a RAM (Random Access Memory) and so forth; and a communication device, and controls entire operations of the imaging section 101. The imaging control section 102 typically controls capturing by the imaging section 101, and generates a captured image on the basis of a signal obtained from the capturing process.

For example, the imaging control section 102 can control the timing of capturing process by the imaging section 101. More specifically, the imaging control section 102 can produce a video by controlling the imaging section 101 so as to continuously shoot images over a predetermined period. Alternatively, the imaging control section 102 can control the imaging section 101 so as to intermittently capture images at predetermined intervals (so-called, time-lapse capturing). Meanwhile, in a case where a plurality of embryos is captured, the imaging control section 102 may directly or indirectly control the incubator I1 so as to move the imaging device 10 or the dish according to the capture timing of the embryos to be captured. Note that an exemplary control of the timing of capturing process according to one embodiment of the present disclosure will be described later.

Alternatively, the imaging control section 102 may control the wavelength, illumination intensity or illumination time of the light source provided to the imaging section 101. For example, the imaging control section 102 may control the light source of the imaging section 101, so as to illuminate embryo with light of appropriate wavelength at minimum illumination intensity, only within a period the imaging section 101 is capturing images. This can minimize phototoxicity on embryo.

Now, the imaging control section 102 may preset a region of interest (ROI) for the image, which will be detailed later. The region of interest in this context means a region subject to image analysis by a kinetic analysis section 203 described later. The region of interest according to the embodiment is an internal region of embryo, and very preferably a region corresponding to cytoplasm of embryo. Preset of the region of interest and so forth will be described later.

The imaging control section 102 outputs the produced images and so forth to the information processing device 20.

Information Processing Device

The information processing device 20 is a device having an image analyzing function. The information processing device 20 may be embodied by various devices having image analyzing function, including PC (Personal Computer), tablet and smartphone. The information processing device 20 contains a processing circuit such as CPU (Central Processing Unit), and a communication device which includes hardware allowed for wireless or wired communication. For example, the information processing device 20 according to the embodiment allows the communication device to acquire a plurality of images (for example, time-lapse images and video) from the imaging device 10. The processing circuit then acquires information regarding each of the still images and video, and determines events regarding embryo using the individual information. The processes performed by the processing circuit of the information processing device 20 are output to a storage device, a display device, or the like provided inside or outside the information processing device 20. Note that the information processing device 20 may be embodied by one or a plurality of information processing devices on a network. A functional configuration for realizing the respective functions of the information processing device 20 will be described below.

Note that, although the information processing system 1 in the embodiment includes the imaging device 10 and the information processing device 20, the present technology is not limited to this design. For example, the imaging device 10 may take part in processing regarding the information processing device 20 (for example, kinetic analysis, feature extraction, individual estimation processes, or determination). In this design, the information processing system 1 is embodies by an imaging device having, for example, a kinetic analyzing function.

Now the embryo, which is a target biological sample to be observed by the information processing system 1 according to the embodiment, will be explained. For example, a normal human fertilized egg shows a pronucleus that appears immediately after fertilization, and then starts cell division. Note that, although the fertilized egg is not an embryo but pronuclear-stage embryo in the strict sense, the present specification will also deal the fertilized egg as one form of embryo.

In cleavage, a normal fertilized egg (embryo) initially in the 1-cell stage cleaves to produce a 2-cell stage embryo, then repeats cleavage to produce a 4-cell embryo, 8-cell embryo, morula, to reach blastocyst finally. In the normal course, the blastocyst adheres to a uterus, the pellucida that surrounds the embryo breaks, and the embryo thus hatches. That is, the timing of cleavage can be deemed to be one checkpoint of embryogenetic stage.

There has been efforts to develop a technique for evaluating such growth of embryo, by capturing images of embryo in a time-series manner, and by estimating an embryogenetic stage using information obtained from the captured images. For example, JP 2016-5098485T discloses a technique by which a plurality of classifiers is applied to the time-series images of embryo to determine classification probability of the embryo, and the embryo is then ranked on the basis of such classification probability. Meanwhile, JP 2013-198503A discloses a technique by which the temporal length of cell division stage is measured using time-lapse images (time-series images captured at long intervals such as 30 minutes), and a quality index of embryo is obtained on the basis of the temporal length of cell division stage.

The above-described techniques predict the embryogenetic stage, by estimating growth of embryo solely from still images. It is, however, difficult for such techniques to track acute morphological changes of embryo, morphological changes in directions other than in-plane direction, and morphological changes not associated with geometrical changes.

Figure 2:
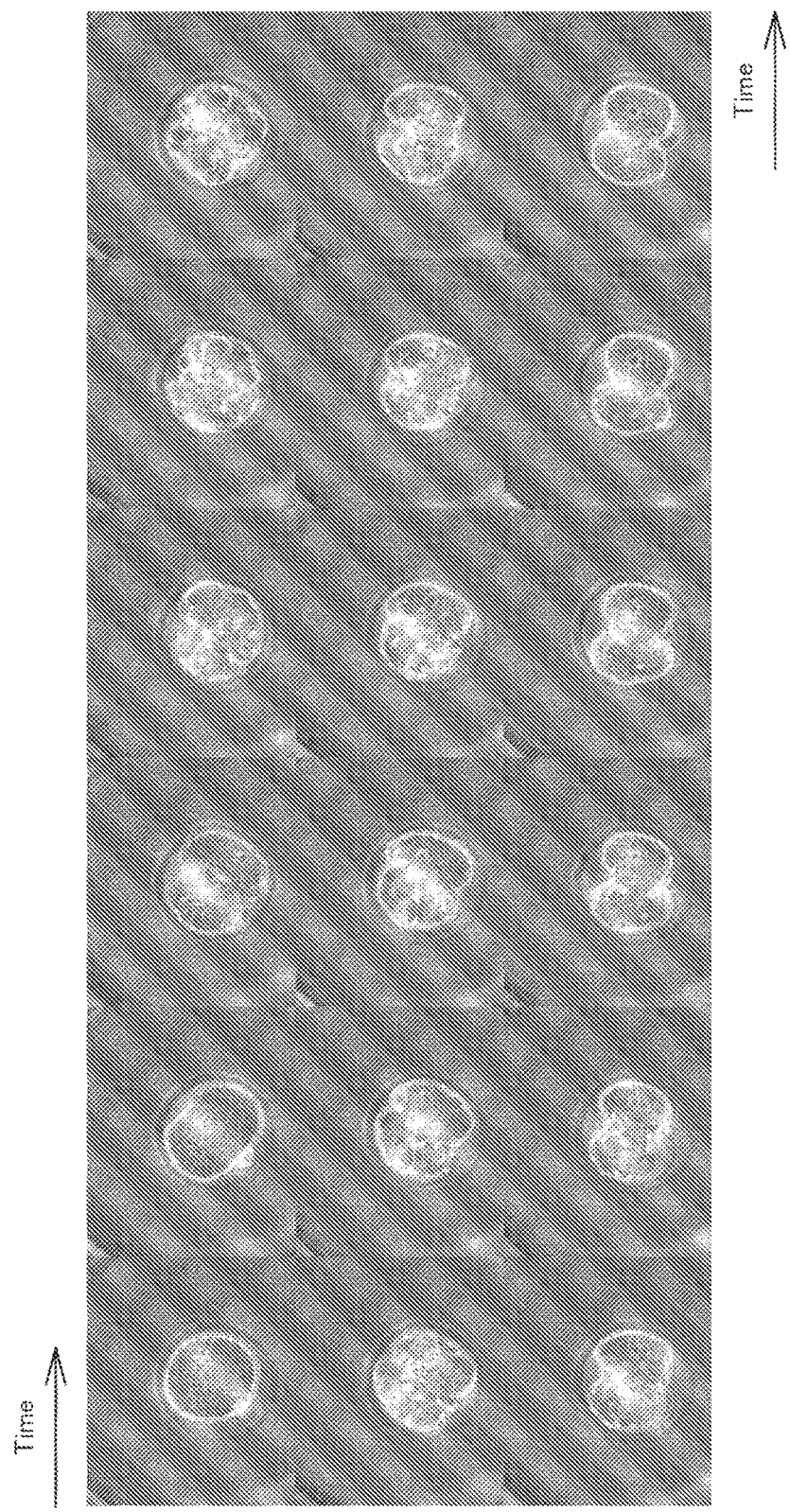
FIG. 2 illustrates a first example of time-lapse images of an embryo at around cleavage from 1-cell stage to 2-cell stage, captured at 15 minute intervals.
Figure 3:
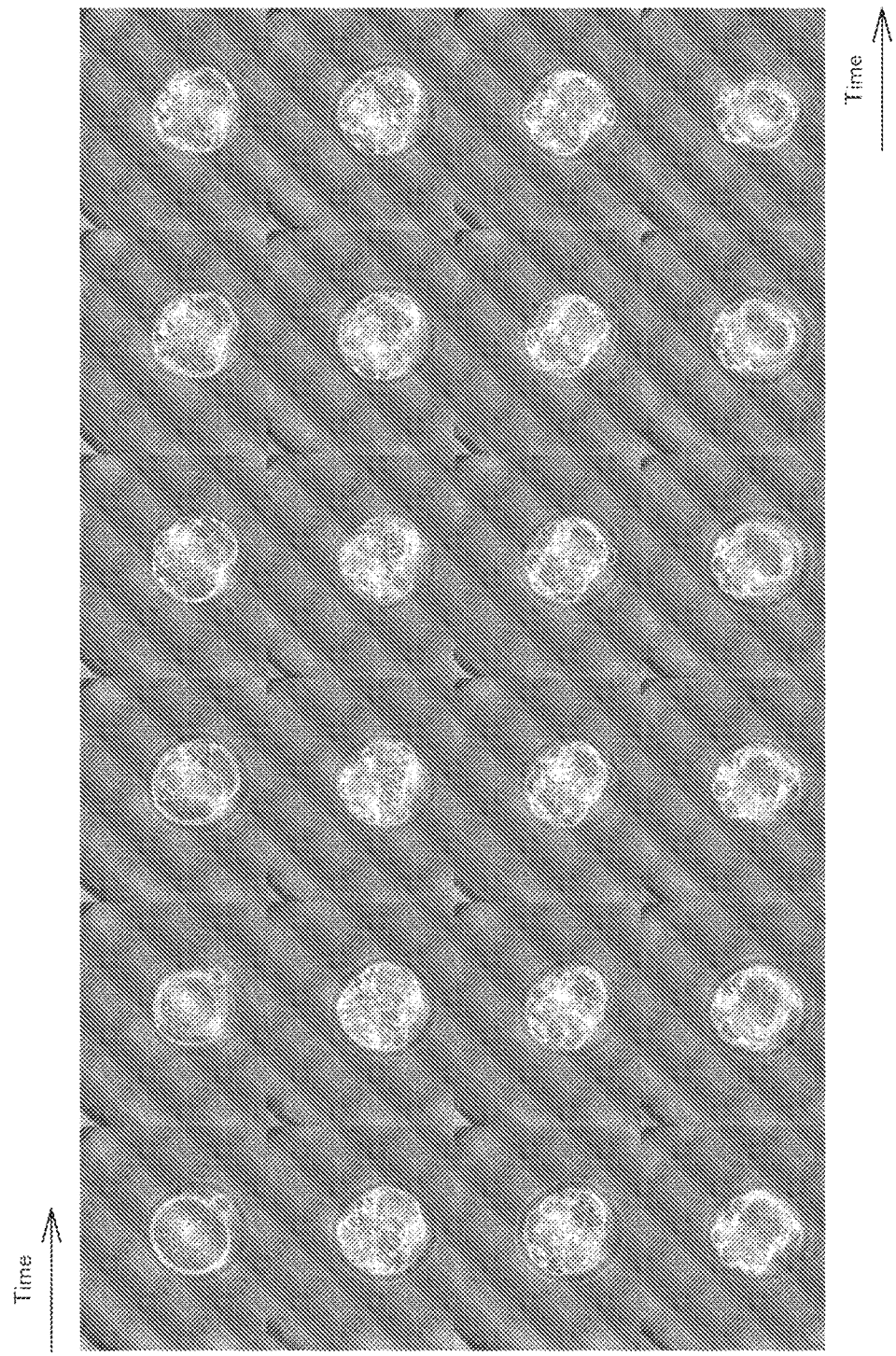
FIG. 3 illustrates a second example of time-lapse images of an embryo at around cleavage from 1-cell stage to 2-cell stage, captured at 15 minute intervals.

FIG. 2 and FIG. 3 illustrate a first example and a second example of time-lapse images of an embryo at around cleavage from 1-cell stage to 2-cell stage, captured at 15 minute intervals. In these plurality of images shown in FIG. 2 and FIG. 3, the frame advances from the left in the upper row towards the right in the lower row. FIG. 2 shows cleavage of embryo in the in-plane direction, making it possible to discriminate the 1-cell stage from the 2-cell stage. Referring however to FIG. 3, the embryo cleaves in the direction other than the in-plane direction, and more specifically in the direction perpendicular to the sheet of drawing, making it difficult to determine the timing of cleavage from the still images. It is naturally difficult to determine occurrence of cleavage from the still images in FIG. 3, since daughter cells overlap in the perpendicular direction.

Alternatively, even if the embryo should cleave in the in-plane direction as illustrated in FIG. 2, the cleavage may fall in a time zone between the frames of still image. If the interval of capturing is long, it is difficult to timely capture the cleavage.

Moreover, depending on individual differences among embryos, not only orientation of morphological changes including cleavage, but also time consumed for the morphological changes may largely vary. Alternatively, even if the morphological changes of embryo should not be so large apparently, any characteristic changes associated with cleavage or so might occur in the cytoplasm of embryo.

The information processing system 1 according to the embodiment is then designed to acquire first information on the basis of a still image in a frame (time-lapse image) corresponding to a predetermined time, from among a plurality of images of a biological sample captured in a time-series manner; to acquire second information on the basis of an interframe change of the plurality of images (video) in a predetermined period; and to determine an event regarding the biological sample, using these information. As will be described in the embodiments, the first information contains features obtained from each of the time-lapse images, or information obtained on the basis of such feature, and the second information contains kinetic feature obtained from changes in the video within a predetermined period, or information obtained on the basis of such feature. With such design, it becomes possible to correctly and minutely understand events such as morphological changes in the biological sample, which cannot be determined solely from still images, by combining information regarding features individually obtained from the still images (time-lapse images) and video.

The overview of the information processing system 1 according to one embodiment of the present disclosure has been described above. Now the individual embodiments below will explain exemplary applications of the present technology, focusing embryo as one example of the biological sample. The present technology is, however, not limited to these examples. For example, the information processing system 1 according to the embodiment is also applicable to cell, biotissue and so forth capable of demonstrating morphological changes specific to living bodies, such as those causing cell division, or such as those incorporating other cell or the like. In addition, the events regarding biological sample to which the present technology is applicable, other than cleavage of embryo, can include proliferation and division of cancer cell or other cells, and morphological changes of immunocyte and other cells. In addition, a target of application of the information processing system 1 according to the embodiment may be animal, plant or inanimate structure. For example, a target to be observed whose structure or geometry can change over a period ranging from several hours to several days, such as growth of thin film or nanocluster crystal, can be a target of application of the information processing system 1 according to the embodiment.

The information processing device 20 contained in the information processing system 1 according to one embodiment of the present disclosure is embodied in the embodiment below. Specific examples of configuration and processing of the information processing device 20 will be explained below.

2. First Embodiment

The first embodiment of the present disclosure will be explained below, referring to FIG. 4 to FIG. 14.

2.1. Exemplary Configuration

Figure 4:
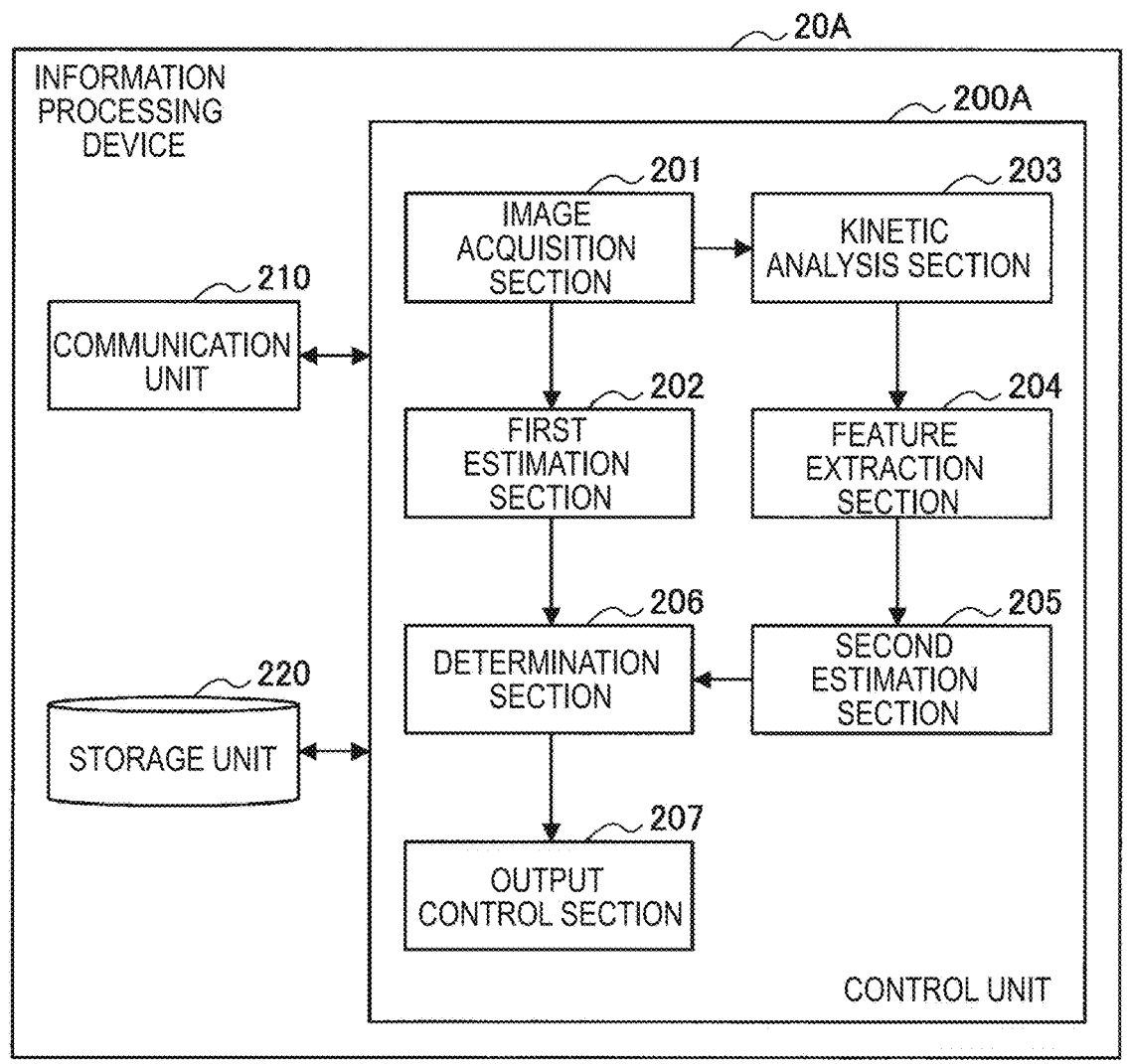
FIG. 4 is a functional block diagram illustrating an exemplary functional configuration of an information processing device according to a first embodiment of the present disclosure.

FIG. 4 is a functional block diagram illustrating an exemplary functional configuration of the information processing device 20A according to the first embodiment of the present disclosure. As illustrated in FIG. 4, the information processing device 20A according to the embodiment has a control unit 200A, a communication unit 210 and a storage unit 220. The individual function units will be explained below.

Control Unit

The control unit 200A controls entire operations of the information processing device 20. Again as illustrated in FIG. 4, the control unit 200A has the individual functions of an image acquisition section 201, a first estimation section 202, a kinetic analysis section 203, a feature extraction section 204, a second estimation section 205, a determination section 206 and an output control section 207, and controls operations of the information processing device 20A according to the embodiment in a leading manner. The functions of the individual functional sections contained in the control unit 200A will be described later. The control unit 200A is typically embodied by a processing circuit such as CPU.

Communication Unit

The communication unit 210 is a communication means possessed by the information processing device 20A, and takes part in various types of communications in a wired or wireless manner, through a network (or directly), with an external device. For example, the communication unit 210 communicates with the imaging device 10. More specifically, the communication unit 210 acquires images produced by the imaging device 10. Alternatively, the communication unit 210 may communicate with a device other than the imaging device 10. For example, the communication unit 210 may send images acquired by the image acquisition section 201, information regarding proposal controlled by the output control section 207, and so forth to an external display device or the like. The communication unit 210 is typically embodied by a communication device such as communication antenna combined with RF (Radio Frequency) circuit (wireless communication), an IEEE 802.15.1 port combined with a transceiver circuit (wireless communication), an IEEE 802.11b port combined with a transceiver circuit (wireless communication), or a LAN (Local Area Network) terminal combined with a transceiver circuit (wired communication).

Storage Unit

The storage unit 220 is a storage device installed in the information processing device 20A and stores information acquired by the communication unit 210, information obtained by the respective function units of the control unit 200A, and the like. Further, the storage unit 220 appropriately outputs the stored information in response to a request from each function unit of the control unit 200A or from the communication unit 210. The storage unit 220 is typically embodied by a magnetic recording medium such as hard disk, or a nonvolatile memory such as flash memory. Alternatively, the storage unit 220 may be embodied for example by an external cloud server or storage. In this design, the information processing device 20A is not necessarily provided with the storage unit 220.

Next, the functions of the respective function units installed in the control unit 200 will be described.

Image Acquisition Section

The image acquisition section 201 has a function for acquiring, from the imaging device 10, a plurality of images regarding embryo captured in a time-series manner in the imaging device 10. Such plurality of images are acquired through the communication unit 210.

The plurality of images in this context mean two types—time-lapse images and video. The time-lapse images are a series of still images obtained by, as described above, intermittently capturing images at predetermined intervals. In other words, a time-lapse image means a still image in a frame corresponding to a predetermined time, among from a plurality of images. The predetermined interval, which is typically several minutes to several tens of minutes for embryo, may suitably be controlled depending on the degree of morphological changes in the biological sample to be observed.

Meanwhile, the video contains images in a plurality of successive frames obtained by continuous image shooting over a predetermined period. Such video may be a video obtained by seamless image shooting that takes place from the start through the end of shooting, but may preferably be a video obtained by continuous image shooting that takes place only for a predetermined period, and at predetermined intervals, taking phototoxicity and image processing load into consideration. In this embodiment, the plurality of images that compose the video can be those produced by continuous image shooting that takes place over several seconds to several tens of seconds, at a frame rate of several frames per second.

Note that the image may be image(s) regarding one or a plurality of embryos. The image(s) regarding the plurality of embryos mean images that contain the plurality of embryos one by one in imaging frames, or an image that contains the plurality of embryos in a single imaging frame.

The image acquisition section 201 acquires an image that contains embryo captured, for example, by the imaging section 101 of the imaging device 10. More specifically, the image acquisition section 201 may acquire an image containing embryo, which is captured in a real-time manner by the imaging section 101 of the imaging device 10, through the communication unit 210. This design enables real time execution of the individual processing for determining events regarding the embryo, in the individual functional sections in the succeeding stage. Alternatively, the image acquisition section 201 may acquire, from the storage unit 220, an image which has preliminarily been captured by the imaging section 101 of the imaging device 10 and stored in the storage unit 220. With such design, it now becomes possible to carry out a process for determining event regarding the preliminarily captured embryo, as post processing.

Figure 5:
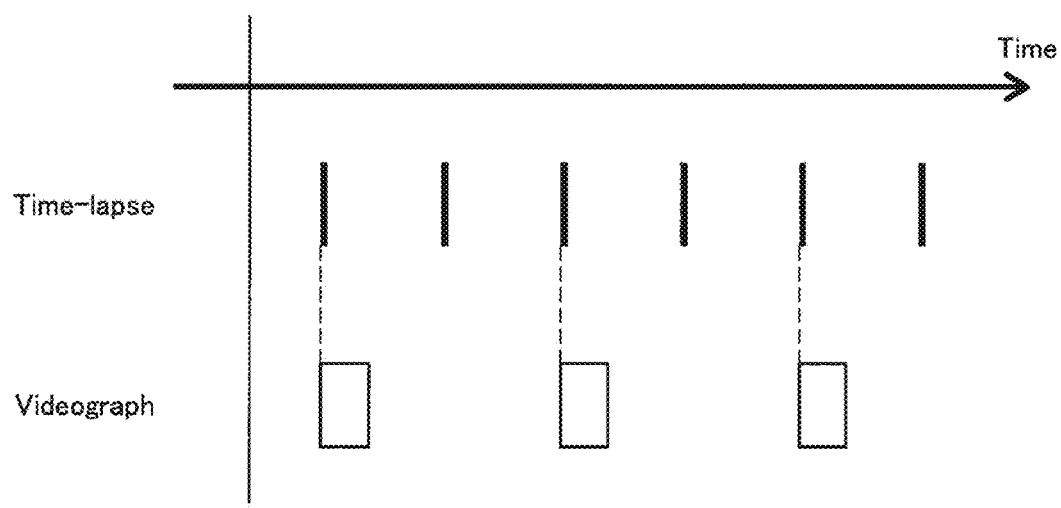
FIG. 5 is a chart explaining capture timing of the time-lapse images and videos acquired by the image acquisition section according the embodiment.

Note that the time-lapse images and video acquired by the image acquisition section 201 are preferably correlated to the capture timing. FIG. 5 is a chart explaining capture timing of the time-lapse images and video acquired by the image acquisition section 201 according the embodiment. As illustrated in FIG. 5, both of the time-lapse images (Time-lapse) and video (Videograph) acquired by the image acquisition section 201 in the embodiment are captured at predetermined intervals. It is specially noted that, as illustrated in FIG. 5, start time of video shooting agrees with the capture time of the time-lapse images. By using the images thus captured according to such capture timing, it now becomes possible to more accurately correlate, in the succeeding process, the first information obtained on the basis of time-lapse images with the second information obtained on the basis of interframe changes in video.

Note that the capture timing, illustrated in FIG. 5 as a timing controlled by the imaging control section 102, may alternatively be acquired by the image acquisition section 201 by extracting the time-lapse images and video captured at times illustrated in FIG. 5, among from a plurality of images produced by the imaging device 10. Still alternatively, an image for example in the first frame, among from the plurality of images that compose the video shot over a predetermined period, may be used as the time-lapse image. Note that the capture timing illustrated in FIG. 5 is merely for illustrative purposes, and is not specially limited so long as any one of the capture time of the time-lapse images nearly agrees with the start time of video shooting. "Nearly agrees with . . . " in this context means that difference between the times is acceptable if the difference is small enough to assume these times to be concurrent, relative to the entire period over which a series of image capturing processes take place. In short, the capture time of time-lapse image need not be strictly simultaneous with the start time of video shooting.

Note that, for improved accuracy in the individual processes in the succeeding stage, the image acquisition section 201 may properly perform calculation or the like, so as to correct the acquired image for example by interpolation, noise reduction, or rotation.

The image acquisition section 201 outputs, among from the acquired plurality of images, the time-lapse images to the first estimation section 202, and output the video to the kinetic analysis section 203.

First Estimation Section

The first estimation section 202 has a function for providing first estimation regarding embryo, from the acquired time-lapse images. The first estimation section 202 according to the embodiment is one example of the first information acquisition section. The first estimation section 202 typically performs image analysis of the time-lapse images, and acquires an image feature of the time-lapse images. The image feature typically contains a value based on distribution of pixel-related information, such as a quantified value of luminance of image or a statistical value based on luminance distribution, or luminance histogram or frequency spectrum. The image feature may be acquired by using, for example, any of known image analysis technologies.

Figure 6:
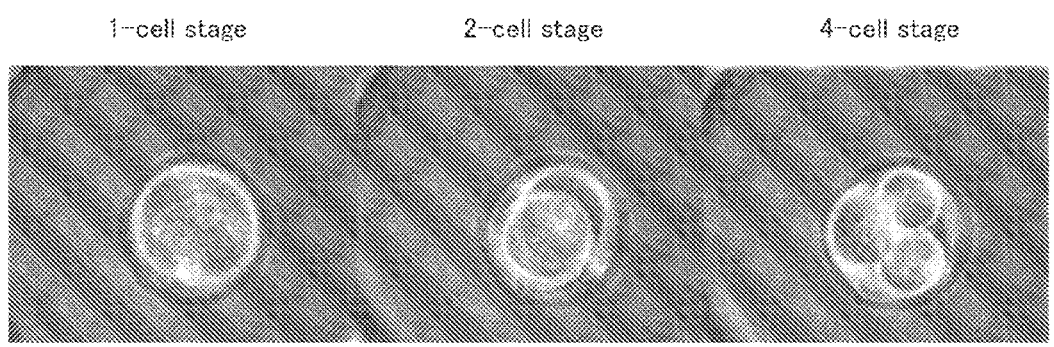
FIG. 6 is a drawing illustrating exemplary images of an embryo corresponding to an embryogenetic stage and the individual cell stages.

Now the first estimation means estimation of embryogenetic stage (that is, to what state of cell stage the embryo belongs). That is, the first estimation is to estimate an embryogenetic stage from morphology of the embryo shown in the time-lapse images. FIG. 6 is a drawing illustrating exemplary images of an embryo corresponding to the embryogenetic stage and individual cell stages. As illustrated in FIG. 6, uncleaved embryo and cleaved embryos are respectively shown in 1-cell stage, 2-cell stage and 4-cell stage.

The first estimation section 202 according to the embodiment performs first estimation by applying acquired results of image analysis, to a learned model that has learned a preliminarily acquired relation between the event regarding embryo and captured image regarding embryo. The learned model is a model constructed typically by using an event regarding embryo as a response variable, and using the result of image analysis regarding embryo as an explanatory variable. Technique regarding such learning may be any of known techniques, such as a neural network based on deep learning or the like. By properly performing the first estimation for each of the acquired time-lapse images, obtainable is an estimation result (first estimation result) regarding the embryogenetic stage shown by each of the stage time-lapse images. Such first estimation result may be an estimation result that indicates to what embryogenetic stage each of the time-lapse images corresponds, or an estimation result that indicates probability that each of the embryogenetic stages shown in the time-lapse images corresponds to any of the cell stages.

Note that the first estimation result regarding embryo is not limited to the above-described classification of cell stages. For an exemplary case where phases immediately before and immediately after cleavage can be discriminable within a single cell stage, the first estimation result can indicate that a developmental stage belongs to early phase or late phase in the cell stage. Meanwhile, for a case where a biological sample other than embryo is applied to the present technique, the first estimation will be to estimate an index that indicates an event regarding the biological sample on the basis of the time-lapse images.

The first estimation section 202 outputs the first estimation result to the determination section 206.

Kinetic Analysis Section

The kinetic analysis section 203 has a function for analyzing kinetics of embryo on the basis of an interframe change of the acquired video. More specifically, the kinetic analysis section 203 presets a region of interest corresponding to the embryo for each frame of video, and analyses changes in the region of interest on the plurality of images. The kinetics in this context means not only autonomous motion of embryo, but also morphological changes in the cytoplasm of embryo.

The region of interest means a region to be analyzed in the succeeding process, in an occupied area of the image. The region of interest according to the embodiment is a region corresponding to the inside of embryo contained in the image. The inside of embryo may specifically mean the cytoplasm contained in a central part of embryo. With such design, it now becomes possible to specify motion of the embryonic cytoplasm by an analytical process or the like in the succeeding stage. Note that, for an exemplary case where also geometrical changes in embryo need be analyzed, the region of interest may be defined not only by cytoplasm, but also by pellucida (a part assumed as an interface to the outside field).

The kinetic analysis section 203 may preset the region of interest, typically according to operation by the user made on an unillustrated input device (for example, known input devices such as mouse, touch pen and touch panel). Alternatively, the kinetic analysis section 203 may preset the region of interest, by using freely selectable image analysis technologies typically based on known algorithms including image thresholding, Hough transformation and machine learning. Still alternatively, the kinetic analysis section 203 may preset the region of interest for a plurality of images, by estimating how the region of interest preset to a single image can move over the plurality of images, using an algorithm such as optical flow. With such design, it now becomes possible to automatically preset the region of interest for the plurality of images in which the motion inside the embryo will be analyzed.

Alternatively, processes for presetting the region of interest for video may, for example, be performed preliminarily by other device having information processing function, such as the imaging device 10. In this case, the function of the kinetic analysis section 203, regarding presetting of the region of interest, may be left unused.

The kinetic analysis section 203 has a function for analyzing changes in the preset region of interest regarding embryo, over the plurality of images. The changes in the region of interest, over the plurality of images, mean motion within the region of interest, or morphological changes in the region of interest, for example. The motion within the region of interest means a motion arising from a motion inside the embryo (cytoplasm) that corresponds to the region of interest. The morphological changes in the region of interest mean geometrical changes in embryo that corresponds to the region of interest, or modal changes inside the embryo. Analytical results on these changes in the region of interest are acquired in a time-series manner as kinetic features.

These kinetic feature include, for example, a feature based on morphological changes in the region of interest, a feature based on motion within the region of interest, and a feature based on changes in pixel information of the image.

The feature based on morphological changes in the region of interest is exemplified by area, circumferential length, long axial length or short axial length of the region of interest; and, changes in average, dynamic range or standard deviation of luminance. Meanwhile, the feature based on motion within the region of interest is exemplified by average, acceleration, standard deviation, travel range, maximum value, minimum value and median of motion within the region of interest. Meanwhile, the feature based on changes in pixel information of the image is exemplified by the amount of change in luminance histogram or frequency spectrum.

The feature employed in the embodiment is based on an average of total motion size in the region of interest. For improved accuracy, the kinetic feature may alternatively be the motion size weighted, for example, by temporal changes in motion direction, or by a statistical value such as standard deviation of the motion size.

Such kinetic analysis can be performed using any of known techniques. For example, motion vector may be analyzed in order to calculate the motion size within the region of interest. The motion vector can be acquired using any of known algorithms such as block matching method or gradient method. Alternatively, morphological changes and so forth in the region of interest may be analyzed by any of known techniques, on the basis of pixel information of the image.

Figure 7:
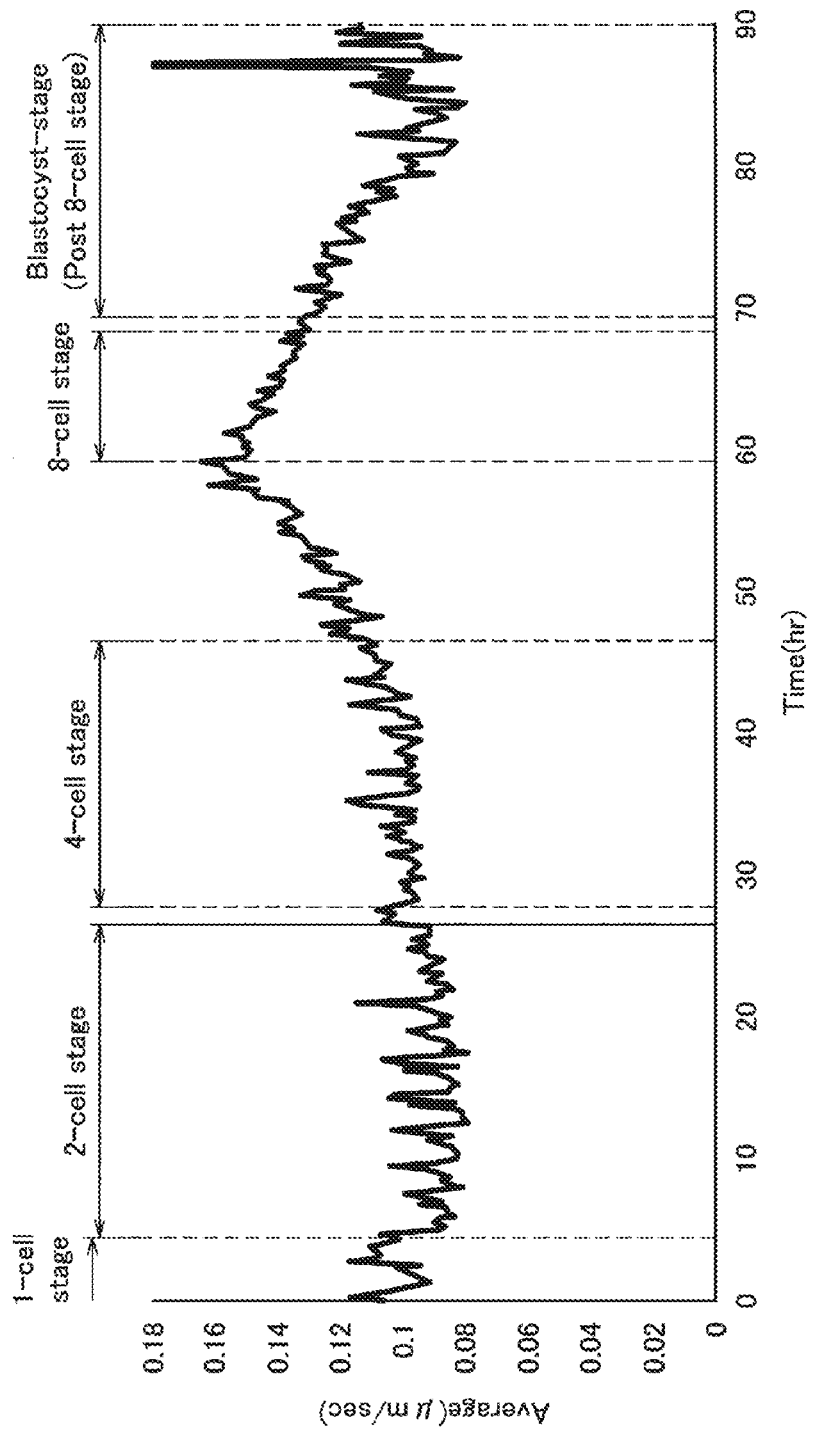
FIG. 7 is a graph illustrating exemplary temporal changes in motion size analyzed by a kinetic analysis section according to the embodiment.

FIG. 7 is a graph illustrating exemplary temporal changes in motion size analyzed by a kinetic analysis section 203 according to the embodiment. The graph in FIG. 7 illustrates time-series data of motion size (an exemplary kinetic feature) in a period from the start of image capturing upon egg fertilization until after 90 hours. Note that the time-series data illustrated in FIG. 7 represents averages of the total motion size in the region of interest taken at predetermined intervals. On the background of the graph, indicated are spans of cell stages of embryo for reference.

The kinetic analysis section 203 outputs the kinetic features obtained by the kinetic analysis to the feature extraction section 204.

Feature Extraction Section

The feature extraction section 204 has a function for extracting, from the thus acquired time-series data of kinetic feature, information to be used by the second estimation section 205 described later, according to predetermined conditions. More specifically, the feature extraction section 204 according to the embodiment extracts, from the time-series data of kinetic feature, a waveform of kinetic feature at a time point which may be a possible option for timing at which the embryo may cleave.

For example, the embryo reportedly shows characteristic vibration attributable to cleavage (cell division) from the 1-cell stage to the 2-cell stage. The embryo in the 2-cell stage also reportedly shows vibration which is considered to arise from expression of egg-derived genes. By extracting the wavelength of kinetic feature attributable to such characteristic feature from the time-series data, it now becomes possible to narrow down the possible options for timing at which specific event regarding embryo, such as embryonic cleavage, is deemed to occur.

The feature extraction section 204 may also determine a waveform of the kinetic feature to be extracted, on the basis of temporal changes in the kinetic feature. For example, the feature extraction section 204 may extract, by peak detection, a peak that satisfies predetermined conditions. Alternatively, the feature extraction section 204 may extract a waveform of kinetic feature assumable as a possible option, by detecting a waveform corresponding to a predetermined frequency obtained after Fourier transformation of the time-series data of kinetic feature. Still alternatively, a waveform of kinetic feature assumable as a possible option may be extracted by correlation analysis of waveform. The feature extraction section 204 can extract a waveform of kinetic feature assumable as a possible option, also by using other known techniques. The waveform of kinetic feature to be extracted can be a waveform depicted by the time-series data of kinetic feature that falls in a time window of a predetermined size. With such design, it now becomes possible to perform second estimation on the basis of waveform pattern, in the second estimation section 205 in the succeeding stage.

Figure 8:
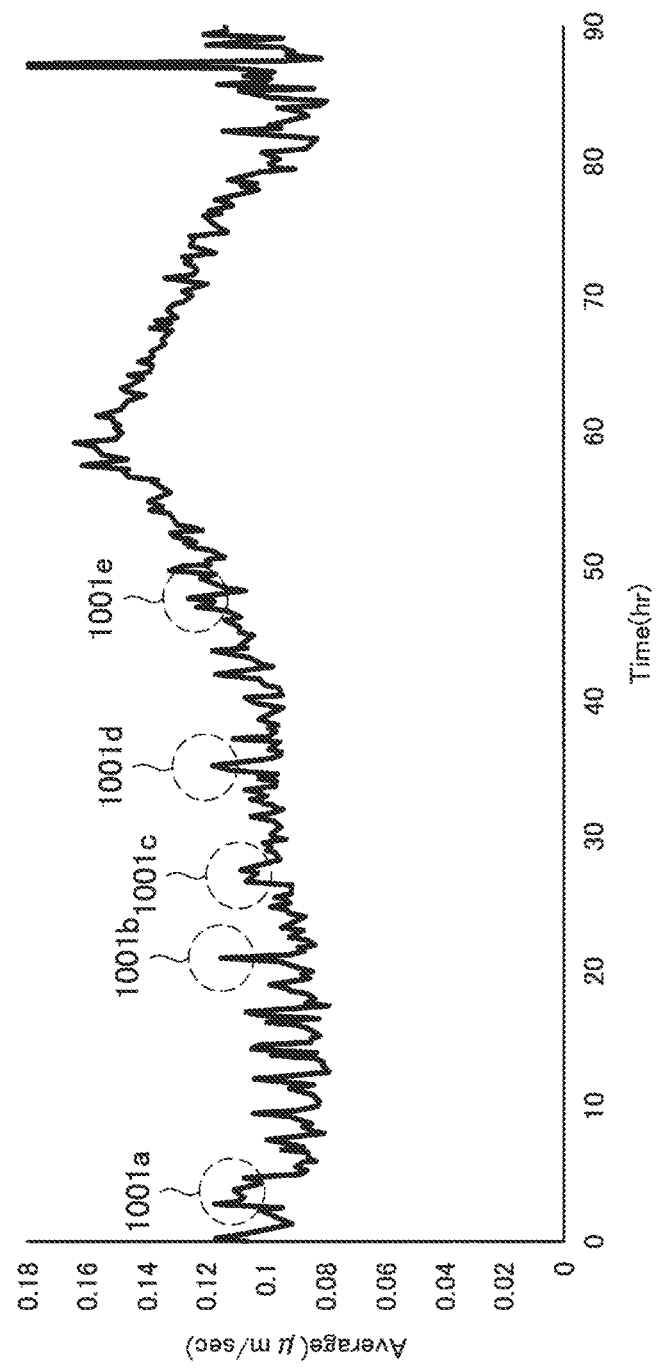
FIG. 8 is a drawing illustrating an exemplary extraction process performed by a feature extraction section according to the embodiment.

FIG. 8 is a drawing illustrating an exemplary extraction process performed by a feature extraction section 204 according to the embodiment. All of the extracted peaks 1001a to 1001e are peaks containing waveforms that satisfy predetermined conditions. As described above, these waveforms are considered to correspond either to an event attributable to morphological changes in embryo in the individual cell stages, or to an event attributable to embryonic morphology found in a transient phase in the cell stage, such as cleavage. The extracted peaks are, however, not always attributable to occurrence of specific events of embryo, leaving open the possibility for incidental noise pickup.

Figure 9:
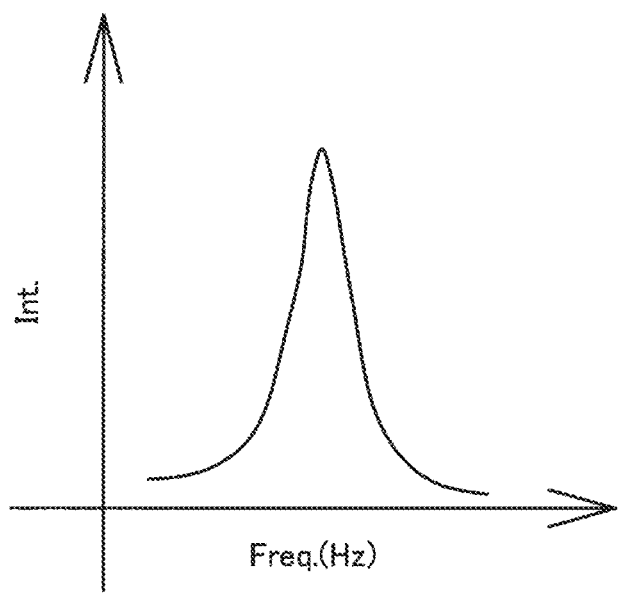
FIG. 9 illustrates an exemplary frequency spectrum obtained after Fourier transformation of a waveform of kinetic feature.

Alternatively, the feature extraction section 204 may further analyze the extracted waveform to extract a waveform feature, and may output the feature. In this case, the waveform feature corresponds to an example of second information. The waveform feature may typically be peak position, peak intensity or peak width in a frequency spectrum obtained after Fourier transformation of the extracted waveform. FIG. 9 illustrates an exemplary frequency spectrum obtained after Fourier transformation of a waveform of kinetic feature. Such waveform feature obtained from the frequency spectrum can be used for the second estimation by the second estimation section 205 in the succeeding stage.

The feature extraction section 204 outputs the information regarding, for example, the waveform of extracted kinetic feature to the second estimation section 205.

Second Estimation Section

The second estimation section 205 has a function for performing second estimation regarding embryo, on the basis of information regarding the waveform of the extracted kinetic feature. The second estimation section 205 according to the embodiment is an example of the second information acquisition section. The second estimation section 205 typically determines a possible option for timing of cleavage, on the basis of information regarding the waveform of the extracted kinetic feature. In other words, the second estimation is to classify the kinetic feature acquired by kinetic analysis of video, into a possible option for timing of cleavage of embryo. The possible option for timing of cleavage typically includes cleavage in association with transition from the 1-cell stage to the 2-cell stage, and cleavage in association with transition from the 2-cell stage to the 4-cell stage.

The second estimation section 205 according to the embodiment performs the second estimation by applying the waveform of the acquired kinetic feature, to a learned model that has learned a preliminarily acquired relation between the event regarding embryo and (the waveform of) the kinetic feature. The learned model can be a model constructed typically by using an event regarding embryo as a response variable, and using the waveform of kinetic feature as an explanatory variable. Also technique regarding such learning may be any of known techniques, similarly as done by the first estimation section 202. By performing the second estimation for each of the waveforms of the extracted kinetic feature, obtainable is an estimation result (second estimation result) regarding timing at which the cleavage was estimated to occur. Such second estimation result may be an estimation result that indicates to what cleavage timing does each of the waveforms of the kinetic feature correspond or not, or may be an estimation result that indicates probability that each of the waveform of the kinetic features corresponds to each of the timings of cleavage.

Figure 10:
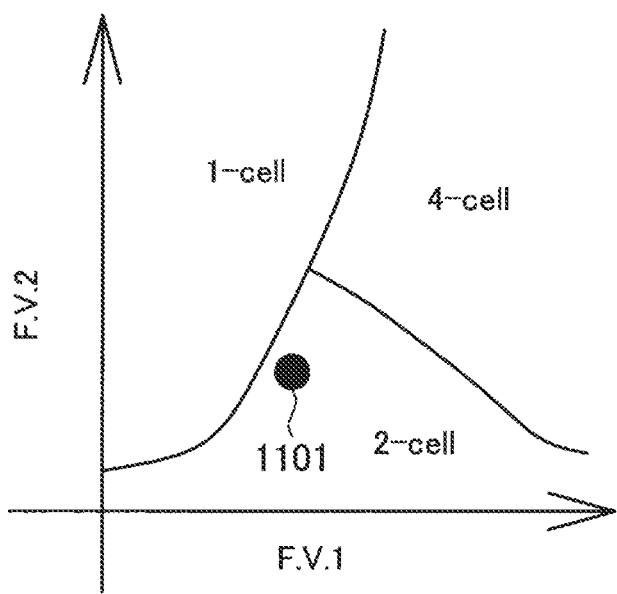
FIG. 10 is a graph illustrating an exemplary second estimation process using a feature regarding a waveform obtained from a second estimation section according to the embodiment.

The second estimation section 205, if having acquired a feature regarding the kinetic feature from the feature extraction section 204, may perform the second estimation using such feature. FIG. 10 is a graph illustrating an exemplary second estimation process using a waveform feature obtained from the second estimation section 205 according to the embodiment. As illustrated in FIG. 10, the second estimation section 205, if having acquired a plurality of features regarding waveform, can map the features to obtain the second estimation result. For example, in a typical case illustrated in FIG. 10, the second estimation result appears to be "2-cell stage", as judged from the position of a plot 1101 given by two features (F.V.1, F.V.2). Alternatively, the second estimation section 205 may perform the second estimation using the above-described model that employs the event regarding embryo (embryogenetic stage) as a response variable, and the waveform feature as an explanatory variable.

Note that the second estimation result regarding embryo is not limited to the above-described classification of possible options for timing of cleavage. For an exemplary case where a waveform that corresponds to a characteristic motion shown by an embryo in a specific embryogenic stage is extractable, the second estimation result may be not only the timing of cleavage, but also classification of possible options for cell stage. For another case where a biological sample other than embryo is applied to the present technology, the second estimation will be estimation of an index that represents an event regarding the biological sample on the basis of changes in video.

The second estimation section 205 outputs the second estimation result to the determination section 206.

Determination Section

The determination section 206 has a function for determining the event regarding embryo, using the first information and the second information. In the embodiment, the first information corresponds to the first estimation result, and the second information corresponds to the second estimation result. Again in the embodiment, the event regarding embryo corresponds to the timing of embryonic cleavage. That is, the determination section 206 according to the embodiment determines the timing of embryonic cleavage, using the first estimation result and the second estimation result.

The determination section 206 may determine the timing of embryonic cleavage, typically on the basis of likelihood obtained by collating the first estimation result with the second estimation result. More in detail, the determination section 206 collates a cell stage that corresponds to a developmental stage given by the first estimation result obtained from each time-lapse image, with a possible option for timing of cleavage given by the second estimation result obtained from each waveform of kinetic feature, and determines a possible option whose likelihood will be highest, among from the possible options obtained as the second estimation result, as the timing of cleavage.

For an exemplary case where a time-lapse image is estimated by the second estimation section 205 to represent a possible option for the timing of cleavage from the 1-cell stage to the 2-cell stage, in a time zone where images estimated by the first estimation section 202 to represent either the 1-cell stage or the 2-cell stage are contained together, such possible option is now considered to be most probable as the timing for cleavage. Conversely, even if there were a plurality of possible options for the timing of cleavage from the 1-cell stage to the 2-cell stage, one of the possible options can be considered to be probable as the timing of cleavage, if such one possible option falls in the time zone where estimations of 1-cell stage and 2-cell stage coexist.

It has been difficult in the past to accurately determine the timing of cleavage on the machine basis, referring solely to the time-lapse images, or solely to the results of kinetic analysis, for example due to ambiguity of boundary between a plurality of cell stages, or noise-induced erroneous detection of similar waveforms and consequent multiple extraction of possible options for the timing of cleavage. The determination section 206 according to the embodiment now makes it possible to determine a probable timing for cleavage, by collating the first estimation result and the second estimation result. More specifically, by using, among from a plurality of images regarding the biological sample, information regarding morphology of the biological sample obtained from the still image (image in frame), in combination with information regarding the kinetics of the biological sample obtained from interframe changes in video (plurality of images within a predetermined period), it now becomes possible to clarify an event regarding such biological sample more accurately.

Having described in the embodiment about determination of the timing for embryonic cleavage, as an exemplary determination of the event regarding biological sample, note that the present technology is not limited to such example. Even for a case where the present technology is applied to a biological sample other than embryo, it now becomes possible to accurately determine the event regarding biological sample, which has not been successful enough solely with the time-lapse images or kinetic analysis, by using the first information (first estimation result, etc.) obtained from the time-lapse images of the biological sample, in combination with the second information (second estimation result, etc.) obtained from kinetic analysis. For example, there has been an actual case where the kinetics have changed in a cytoplasm of the biological sample, despite the biological sample apparently seemed to cause no morphological change when judged solely by the time-lapse images. Hence, there were events overlooked as a result of relying solely upon the time-lapse images. In addition, even if the morphological changes obtained from the time-lapse images were apparently similar, it has been difficult to determine whether the changes are attributable to growth of the biological sample, or to degeneration. Now according to the technology of the embodiment, it becomes possible to determine such morphological changes in the biological sample, in a complementary manner from the results of kinetic analysis.

The determination section 206 outputs the result of determination to the output control section 207.

Output Control Section

The output control section 207 has a function for controlling output resulted from processing in the control unit 200A. For example, the output control section 207 can make the storage unit 220 store all or part of the acquired plurality of images, or can output them through the communication unit 210 to an external display device or the like. Alternatively, the output control section 207 can output, as unmodified data, the result of determination given by the determination section 206 to the storage unit 220, or to an external display device or the like, in a visualized form (graph, for example).

2.2. Exemplary Processing

The configuration and the functions of the information processing device 20A according to the embodiment have been described above. Next, an exemplary process performed by the information processing device 20A according to the embodiment will be described referring to FIG. 11.

Figure 11:
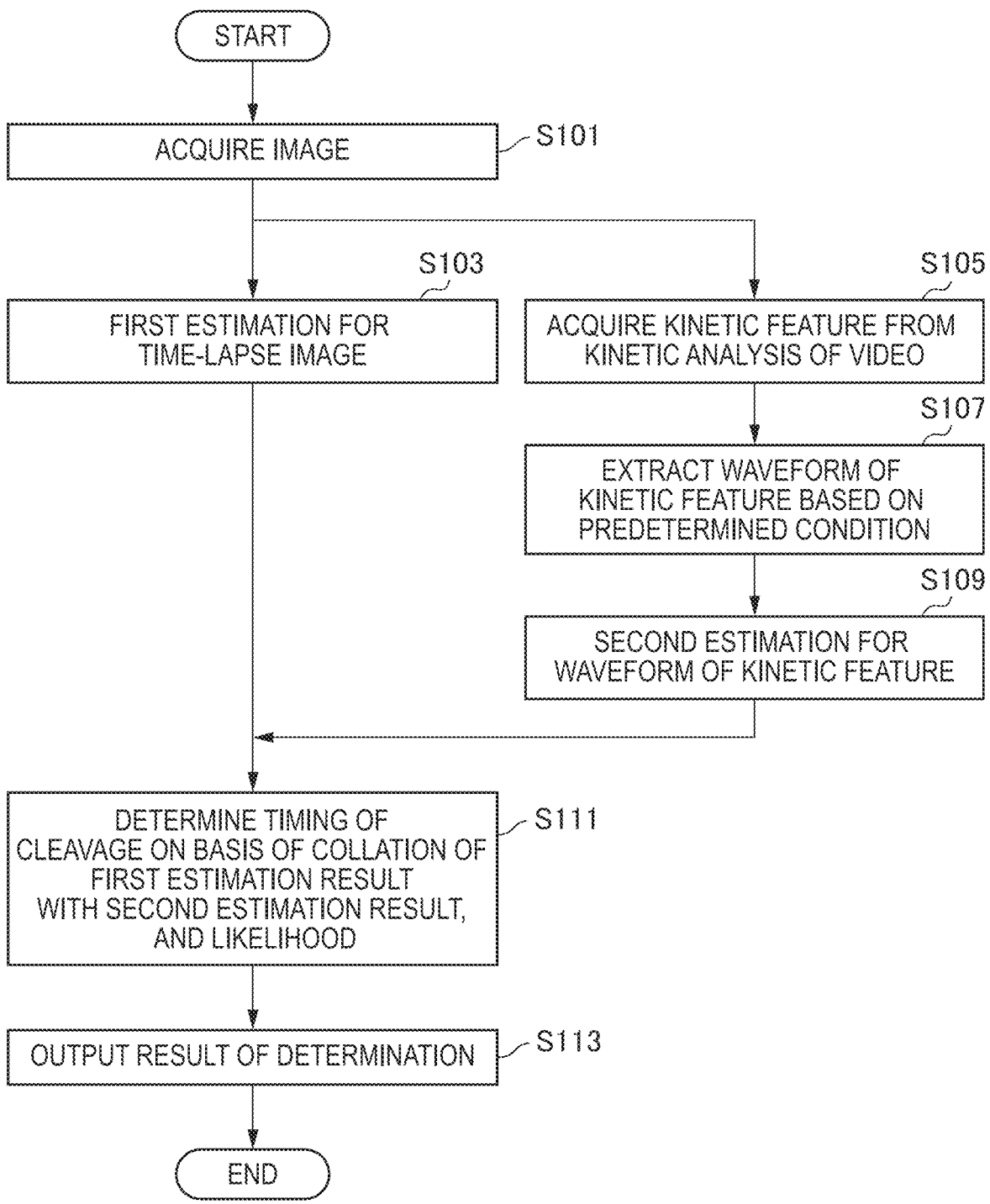
FIG. 11 is a flowchart illustrating an exemplary process performed by an information processing device according to the embodiment.

FIG. 11 is a flowchart illustrating an exemplary process performed by the information processing device 20A, according to the first embodiment of the present disclosure. The flowchart in FIG. 11 illustrates an exemplary process flow in which the information processing device 20A acquires the time-lapse images and video regarding embryo captured in a time-series manner from the imaging device 10, estimates each of the time-lapse images and video, and determines the timing for embryonic cleavage using the estimation results.

First, the image acquisition section 201 acquires the time-lapse images and video regarding embryo captured in a time-series manner, through the communication unit 210 from the imaging device 10 (step S101).

Next, the first estimation section 202 performs the first estimation regarding the acquired time-lapse images (step S103). The first estimation result is output to the determination section 206.

Concurrently with the process in step S103, the kinetic analysis section 203 performs kinetic analysis regarding the video, to acquire time-series data of the kinetic feature (step S105). The feature extraction section 204 then extracts a waveform of the kinetic feature on the basis of predetermined conditions, from the waveform represented by the time-series data of kinetic feature (step S107). The predetermined conditions refer to, as described above, conditions according to which the waveform representing the kinetics of embryo attributable to embryonic cleavage is extracted.

Next, the second estimation section 205 performs the second estimation regarding the waveform of the extracted kinetic feature (step S109). The second estimation result is output to the determination section 206.

Next, the determination section 206 determines a possible option for cleavage, at which the likelihood obtained by collating the first estimation result with the second estimation result becomes highest, as the timing for cleavage (step S111). The output control section 207 then controls output of the acquired determination result and so forth (step S113).

An exemplary processing performed by the information processing device 20A according to the embodiment has been described. Note that the flowchart shown in FIG. 11 illustrates a flow on the premise of post-processing which takes place after all images within a period corresponding to the embryogenetic stage to be observed have been acquired. For example, such process is enabled in a real time manner, by properly repeating the processes in step S101 to S113. Real-time determination of the timing for cleavage will enable early judgment on success or failure of embryonic growth.

The first embodiment of the present disclosure has been described. The first embodiment of the present disclosure is presumed to be particularly effective for a case where data obtained from the kinetic analysis shows some tendency throughout experiments. Such tendency is exemplified by gradual reduction of motion size, and distinct kinetic feature observable upon occurrence of event. For an exemplary case of cell death (apoptosis) of cancer cell, the motion size is known to gradually but clearly decrease, starting from 10 hours before occurrence of event. Moreover, there is also an observation of distinct increase of motion size during morphological change. Note that the first embodiment of the present disclosure demonstrates a significant effect even for a case where only a relatively small volume of data is obtainable from kinetic analysis.

3. Second Embodiment

Next, the second embodiment of the present disclosure will be explained referring to FIG. 12 to FIG. 14. An information processing device 20B according to the embodiment is designed to analyze each of the time-lapse images to acquire an image feature, and to determine an embryogenetic stage and timing for cleavage, on the basis of the image feature regarding the time-lapse images, and the waveform of kinetic feature of video that is contained in a period defined in reference to the capture time of the time-lapse image.

3.1. Exemplary Configuration

Figure 12:
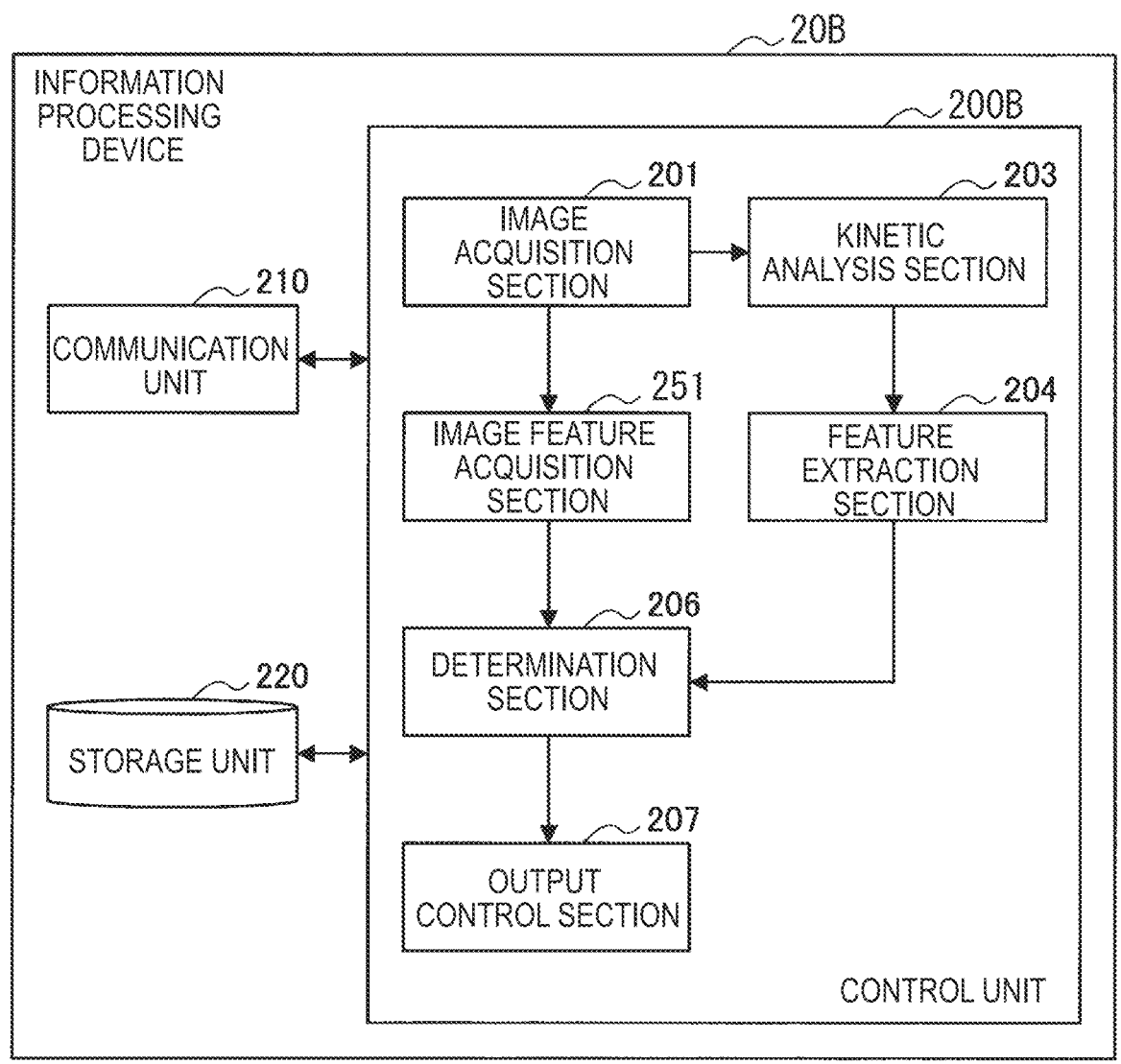
FIG. 12 is a functional block diagram illustrating an exemplary functional configuration of an information processing device according to a second embodiment of the present disclosure.

FIG. 12 is a block diagram illustrating an exemplary functional configuration of the information processing device 20B according to the second embodiment of the present disclosure. As illustrated in FIG. 12, the information processing device 20B according to the embodiment has a control unit 200B, the communication unit 210 and the storage unit 220. Functions of the communication unit 210 and the storage unit 220 are same as those in the first embodiment, and will therefore not be explained again. The image feature acquisition section 251 according to the embodiment is one example of the first information acquisition section, meanwhile the feature extraction section 204 according to the embodiment is an example of the second information acquisition section.

The control unit 200B contains, as illustrated in FIG. 12, the individual functions of the image acquisition section 201, the kinetic analysis section 203, the feature extraction section 204, the determination section 206, the output control section 207 and the image feature acquisition section 251. The embodiment will deal with the image feature acquisition section 251, the feature extraction section 204 and the determination section 206. The functions possessed by the other functional sections are same as those in the first embodiment, and will not be described again.

Image Feature Acquisition Section

The image feature acquisition section 251 has a function for analyzing each of the acquired time-lapse images, and acquiring image feature of time-lapse image for each of the time-lapse images. The image feature typically contains a value based on distribution of pixel-related information, such as a quantified value of luminance of image or a statistical value based on luminance, or luminance histogram or frequency spectrum. The image feature may be acquired by using, for example, any of known image analysis technologies. Such image feature is one example of the first information.

The image feature acquisition section 251 outputs the information regarding the acquired image feature to the determination section 206.

Feature Extraction Section

The feature extraction section 204 according to the embodiment extracts, from the time-series data of kinetic feature acquired from the kinetic analysis section 203, the kinetic feature at the capture time of time-lapse image. More specifically, the feature extraction section 204 extracts a waveform of kinetic feature that falls in a time window defined in reference to the capture time of time-lapse image. Such (waveform of) kinetic feature is an example of the second information.

Figure 13:
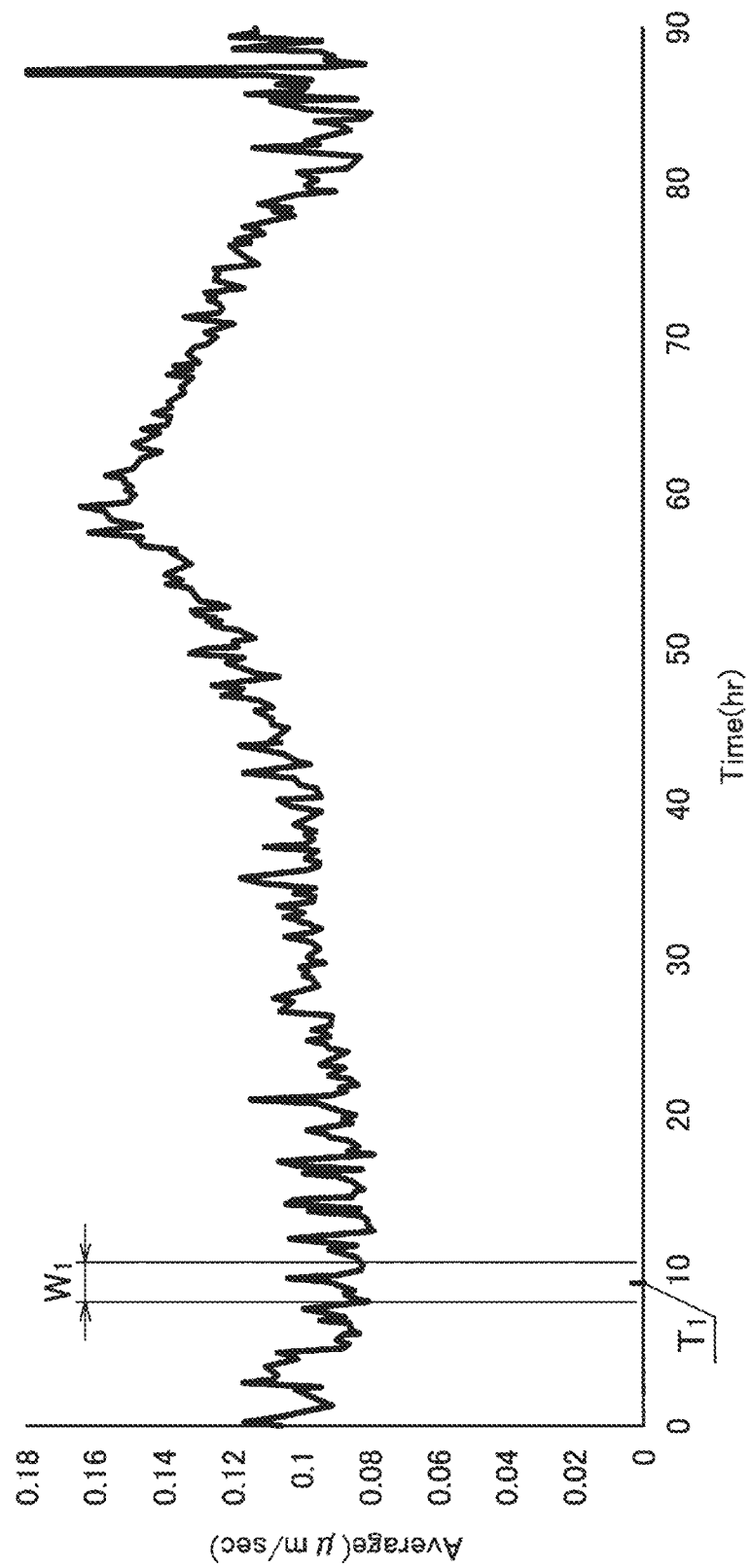
FIG. 13 is a drawing explaining a function of a feature extraction section according to the embodiment.

FIG. 13 is a drawing explaining a function of a feature extraction section 204 according to this embodiment. The graph shown in the drawing is identical to the graphs shown in FIG. 7 and FIG. 8. The feature extraction section 204 extracts a waveform of kinetic feature that falls in a time window W1 defined in reference to the capture time T1 of time-lapse image. Size of the time window W1 is not specifically limited, but is preferably large enough to reasonably acquire a waveform profile.

The feature extraction section 204 may extract a waveform of kinetic feature that falls in a time window defined in reference to each capture time of time-lapse image, and may output the extracted waveform to the determination section 206. Alternatively, the feature extraction section 204 may further analyze the extracted waveform, may extract a feature regarding waveform, and may output the feature. In this case, the waveform feature corresponds to the second information. The waveform feature may typically be peak position, peak intensity or peak width in a frequency spectrum obtained after Fourier transformation of the extracted waveform. Note that such analysis may take place in the determination section 206 in the succeeding stage.

Determination Section

The determination section 206 according to the embodiment determines an event regarding embryo, on the basis of image feature (first information), and waveform of kinetic feature or the like (second information) which are combined into one cluster.

For example, the determination section 206 determines an event regarding embryo, by applying the acquired image feature and kinetic feature or the like, to a learned model that has learned a preliminarily acquired relation between the event regarding embryo, and the image feature and kinetic feature or the like. The learned model can specifically be a model constructed by using an event regarding embryo as a response variable, and using a waveform of image feature and kinetic feature (or waveform feature) as an explanatory variable. Technique regarding such learning may be any of known techniques, such as a neural network based on deep learning or the like.

The event regarding embryo can typically be an index or the like which represents a cell stage representing an embryogenetic stage, and state of embryo. More specifically, the event regarding embryo is exemplified by 1-cell stage, 2-cell stage, 3-cell stage, 4-cell stage, blastocyst, degeneration embryo and so forth. By determining these events at every capture time of the time-lapse images, the boundary at which the event changes may be determined as the timing for embryonic cleavage.

According to the embodiment, there is provided a technique for determining an event regarding embryo, using the image feature obtained from the time-lapse image, and the kinetic feature corresponding to the capture time of time-lapse image. By comprehensively analyzing the features obtained from morphology and kinetics of embryo, the event regarding embryo can be determined with an improved accuracy.

3.2. Exemplary Processing

The configuration and the functions of the information processing device 20B according to the embodiment have been described above. Next, an exemplary process performed by the information processing device 20B according to the embodiment will be described referring to FIG. 14.

Figure 14:
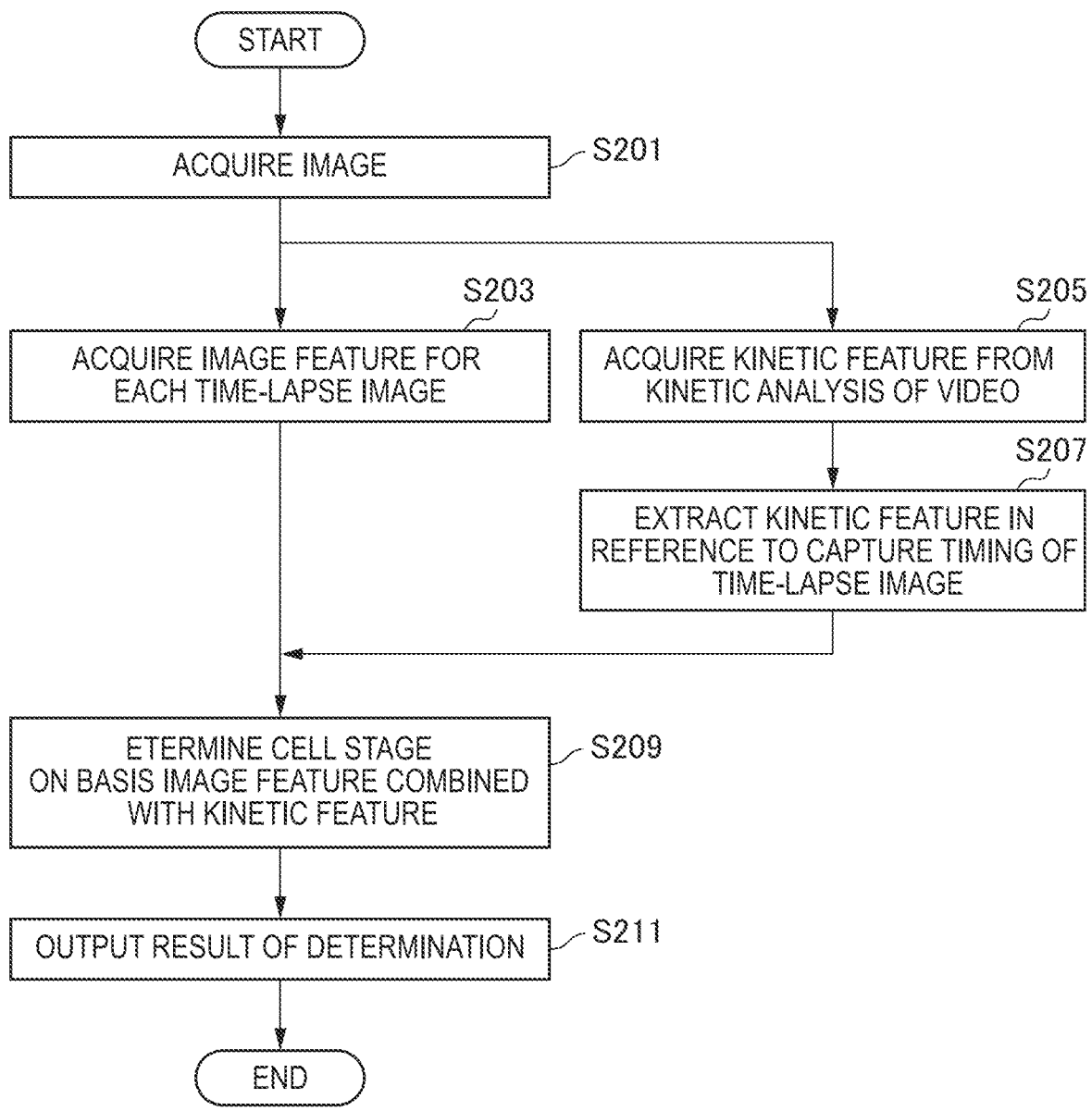
FIG. 14 is a flowchart illustrating an exemplary process performed by an information processing device according to the embodiment.

FIG. 14 is a flowchart illustrating an exemplary process performed by the information processing device 20B, according to the second embodiment of the present disclosure. The flowchart in FIG. 14 illustrates an exemplary process flow in which the information processing device 20B acquires the time-lapse images and video regarding embryo captured in a time-series manner from the imaging device 10, acquires a feature for each of the time-lapse images and video, and determines an embryogenic stage or the like by combining these features.

First, the image acquisition section 201 acquires the time-lapse images regarding embryo captured in a time-series manner and video, through the communication unit 210 from the imaging device 10 (step S201).

Next, the image feature acquisition section 251 acquires an image feature for each of the acquired time-lapse images (step S203). Information regarding the acquired image feature is output to the determination section 206.

Concurrently with the process in step S203, the kinetic analysis section 203 performs kinetic analysis regarding the video, to acquire time-series data of the kinetic feature (step S205). The feature extraction section 204 then extracts a waveform of kinetic feature that falls in a time window defined in reference to the capture time of time-lapse image, from the waveform represented by the time-series data of kinetic feature (step S207). Information regarding the waveform of the extracted kinetic feature is output to the determination section 206.

Next, the determination section 206 determines an embryogenetic stage at each capture time of time-lapse image, on the basis of combination of the image feature and the kinetic feature (step S209). The output control section 207 controls output of the obtained determination result and so forth (step S211).

An exemplary processing performed by the information processing device 20B according to the embodiment has been described. Note that the flowchart in FIG. 14 illustrates a flow on the premise of post-processing which takes place after all images within a period corresponding to the embryogenetic stage to be observed have been acquired. For example, such process is enabled in a real time manner, by properly repeating the processes in step S201 to S211. Real-time determination of the embryogenetic stage will enable early judgment on success or failure of embryonic growth.

The second embodiment of the present disclosure has been explained. The second embodiment of the present disclosure is presumed to be particularly effective for a case where the kinetic feature shows difference between before and after occurrence of the event. The kinetic feature may, for example, be a feature that is observed periodically. For example, kinetic analysis of a fertilized egg, after observed at 15 minute intervals for several days, has suggested a periodical profile of motion size depending on states. Moreover, the second embodiment is also effective for a case where the second estimation is available only with a limited accuracy for various reasons. The reasons are exemplified by weak signal, strong noise, and absence of distinct kinetic feature worthy of the second estimation. Alternatively, it would be difficult in some cases to extract the feature by kinetic analysis, depending on sample conditions. Note that, even for a case where volume and frequency of data acquisition by kinetic analysis are large, the second embodiment can take effects.

4. Third Embodiment

Next, the third embodiment of the present disclosure will be explained referring to FIG. 15 to FIG. 17. An information processing device 20C according to the embodiment is designed to determine an embryogenetic stage and timing for cleavage, on the basis of the first estimation result of an event regarding embryo which has been estimated for each of the time-lapse images, and also on the basis of the second estimation result of an event regarding embryo which has been estimated from a waveform of kinetic feature in video that falls in a period defined in reference to the capture time of the time-lapse image.

4.1. Exemplary Configuration

Figure 15:
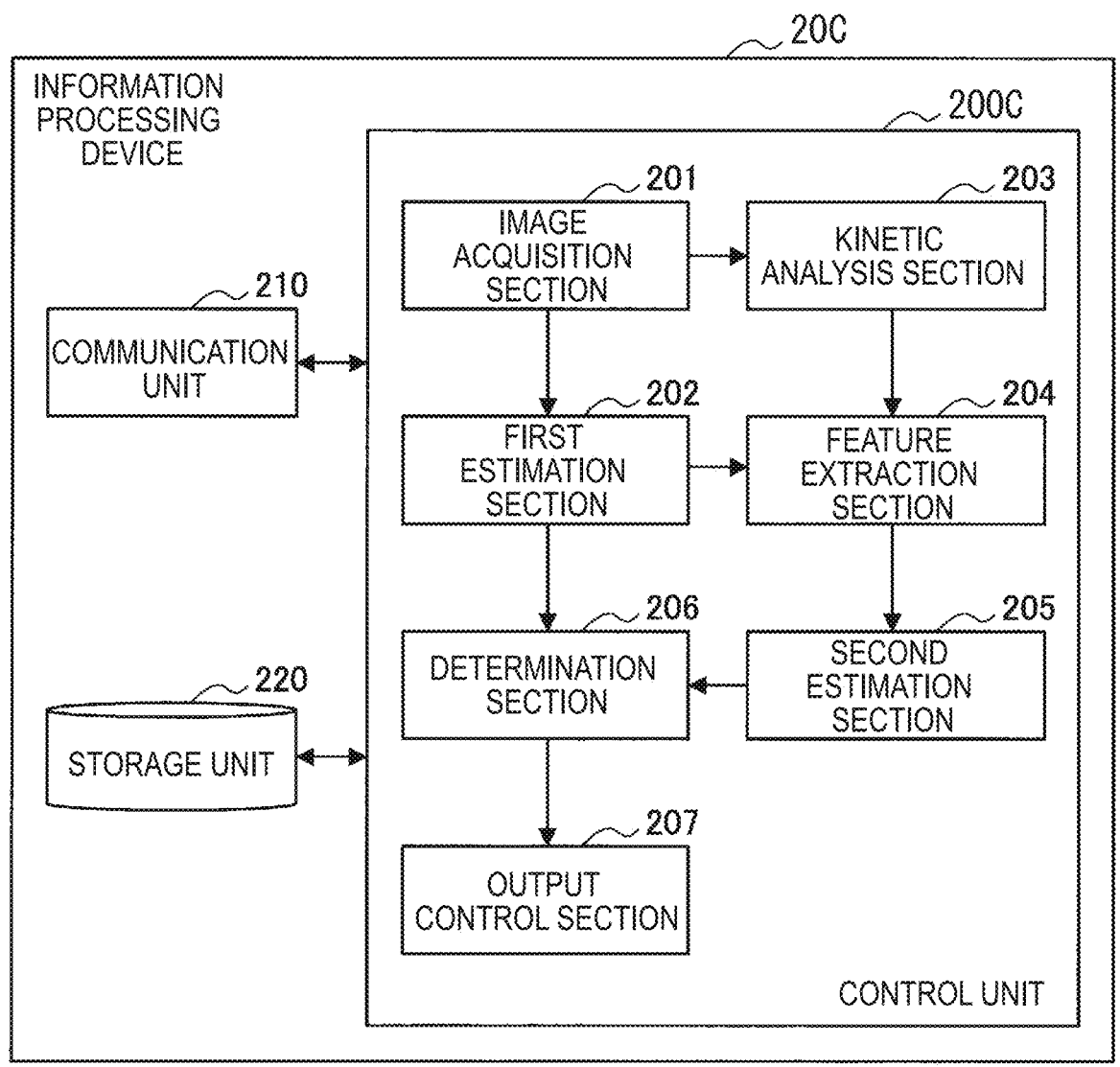
FIG. 15 is a functional block diagram illustrating an exemplary functional configuration of an information processing device according to a third embodiment of the present disclosure.

FIG. 15 is a functional block diagram illustrating an exemplary functional configuration of the information processing device 20C according to the third embodiment of the present disclosure. As illustrated in FIG. 15, the information processing device 20C according to the embodiment has a control unit 200C, the communication unit 210 and the storage unit 220. Functions of the communication unit 210 and the storage unit 220 are same as those in the first embodiment, and will therefore not be explained again.

The control unit 200C has, as illustrated in FIG. 15, the individual functions of the image acquisition section 201, the first estimation section 202, the kinetic analysis section 203, the feature extraction section 204, the second estimation section 205, the determination section 206 and the output control section 207. The embodiment will deal with the first estimation section 202 and the feature extraction section 204. The functions possessed by the other functional sections are same as those in the first embodiment, and will not be described again. Note that the first estimation section 202 according to the embodiment is an example of the first information acquisition section, meanwhile the second estimation section 205 according to the embodiment is an example of the second information acquisition section.

First Estimation Section

The first estimation section 202 estimates, in the same way as in the first embodiment, an event regarding embryo (embryogenetic stage, herein) for each of the time-lapse images. The thus obtained first estimation result is output to the determination section 206. Alternatively, the first estimation result may be output to the feature extraction section 204, as will be detailed later.

Feature Extraction Section

The feature extraction section 204 according to the embodiment extracts, from the time-series data of kinetic feature acquired from the kinetic analysis section 203, the kinetic feature at the capture time of time-lapse image. More specifically, the feature extraction section 204 extracts a waveform of kinetic feature that falls in a time window defined in reference to the capture time of time-lapse image. Such (waveform of) kinetic feature is an example of the second information.

The (waveform of) kinetic feature extracted by the feature extraction section 204 may correspond to the capture time of all time-lapse images, or may correspond to the capture time of part of the time-lapse images. More specifically, the feature extraction section 204 may select a capture time of the time-lapse image to be extracted, on the basis of the first estimation result obtained from the first estimation section 202, and may extract the (waveform of) kinetic feature that corresponds to the selected capture time.

Figure 16:
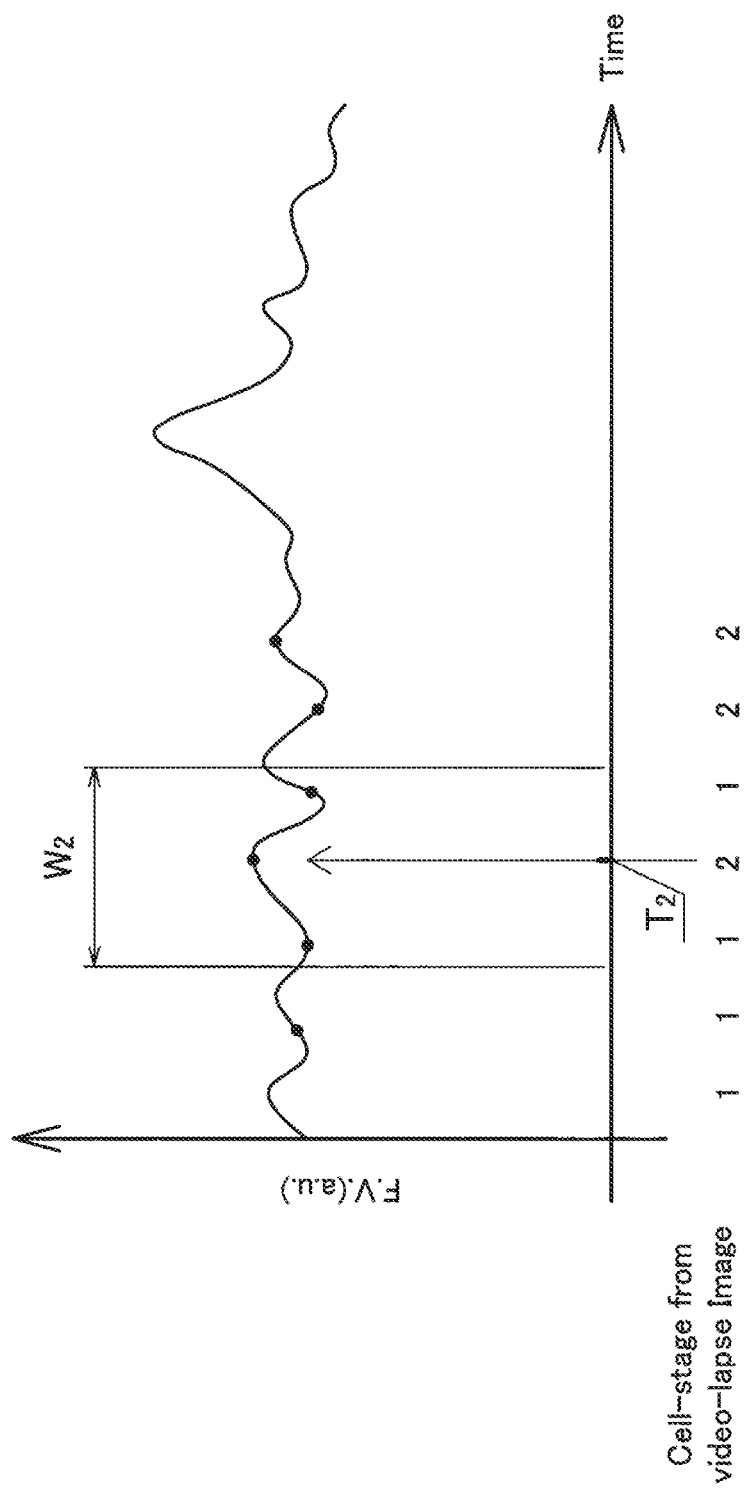
FIG. 16 is a drawing explaining an exemplary extraction process performed by a feature extraction section according to the embodiment.

FIG. 16 is a drawing explaining an exemplary extraction process performed by the feature extraction section 204 according to the embodiment. The graph in FIG. 16 illustrates an example of time-series data of kinetic feature in a period from the start of image capturing upon egg fertilization until after 90 hours. Note that the graph contains, at the bottom, indications of the first estimation (cell stage corresponding to developmental stage) given by the first estimation section 202 for each of the time-lapse images.

The feature extraction section 204 extracts a waveform of kinetic feature that falls in a time window W2 defined in reference to each capture time of time-lapse images, from the time-series data of kinetic feature shown in the graph. Now the feature extraction section 204 may specify a time point for extraction, using the first estimation result obtained by the first estimation section 202. In the example illustrated in FIG. 16, a time point when indication of the first estimation result changed from 1-cell stage to 2-cell stage (or vice versa) may be defined as a time point for extraction. This is because an event such as cleavage is very likely to occur at such time point. Since use of the first estimation result can reduce the number of waveforms of kinetic feature to be extracted, so that process load can be reduced.

Alternatively, the feature extraction section 204 may analyze, in the same way as in the second embodiment, the waveform of the extracted kinetic feature typically by Fourier transformation, to thereby extract a waveform feature. In this case, the waveform feature corresponds to an example of the second information. For example, the waveform feature may be peak position, peak intensity or peak width in a frequency spectrum, as described above. Note that such analysis may take place in the second estimation section 205 in the succeeding stage.

Processes carried out by the second estimation section 205 and the determination section 206 are same as those carried out by the individual functional sections according to the first embodiment. For example, the second estimation section 205 may estimate, on the basis of a waveform of the extracted kinetic feature or the like, a possible option for cleavage as the second estimation result, and the determination section 206 may determine the timing for embryonic cleavage on the basis of the first estimation result and the second estimation result.

According to the embodiment, there is provided a technique for determining an event regarding embryo, using information estimated from the time-lapse images, and the kinetic feature that corresponds to the capture time of the time-lapse image. In addition, by using the information estimated from the time-lapse images in order to extract the kinetic feature, it now becomes possible to analyze only time zones in which cleavage is highly probable to occur, relieving the process load in the information processing system 1.

4.2. Exemplary Process

The configuration and the functions of the information processing device 20C according to the embodiment have been described above. Next, an exemplary process performed by the information processing device 20C according to the embodiment will be described referring to FIG. 17.

Figure 17:
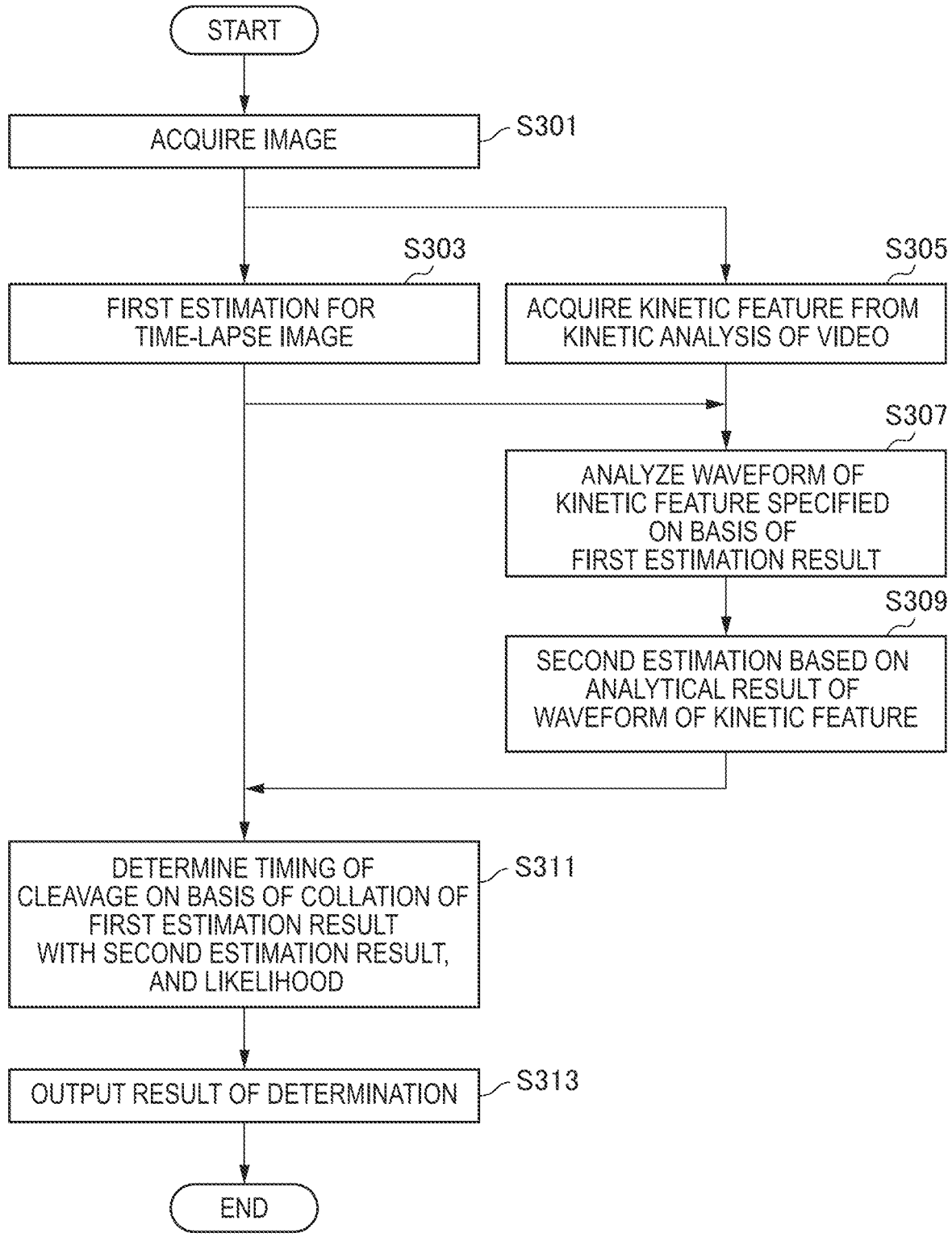
FIG. 17 is a flowchart illustrating an exemplary process performed by an information processing device according to the embodiment.

FIG. 17 is a flowchart illustrating an exemplary process performed by the information processing device 20C, according to the third embodiment of the present disclosure. The flowchart in FIG. 17 illustrates an exemplary process flow in which the information processing device 20C acquires the time-lapse images and video regarding embryo captured in a time-series manner from the imaging device 10, estimates each of the time-lapse images and video, and determines the timing for embryonic cleavage using the estimation results.

First, the image acquisition section 201 acquires the time-lapse images regarding embryo captured in a time-series manner and video, through the communication unit 210 from the imaging device 10 (step S301).

Next, the first estimation section 202 performs the first estimation regarding the acquired time-lapse images (step S303). The first estimation result is output to the feature extraction section 204 and the determination section 206.

Concurrently with the process in step S303, the kinetic analysis section 203 performs kinetic analysis regarding the video, to acquire time-series data of the kinetic feature (step S305). The feature extraction section 204 then extracts a waveform of the kinetic feature, from the waveform represented by the time-series data of kinetic feature (step S307). Now in the embodiment, extracted is a waveform of kinetic feature of video which falls in a period defined in reference to a time point (capture time of time-lapse image) specified on the basis of the first estimation result.

Next, the second estimation section 205 performs the second estimation regarding the waveform of the extracted kinetic feature (step S309). The second estimation result is output to the determination section 206.

Next, the determination section 206 determines a possible option for cleavage, at which the likelihood obtained by collating the first estimation result with the second estimation result becomes highest, as the timing for cleavage (step S311). The output control section 207 then controls output of the acquired determination result and so forth (step S313).

An exemplary processing performed by the information processing device 20C according to the embodiment has been described. Note that the flowchart in FIG. 17 illustrates a flow on the premise of post-processing which takes place after all images within a period corresponding to the embryogenetic stage to be observed have been acquired. For example, such process is enabled in a real time manner, by properly repeating the processes in step S301 to S313. Real-time determination of the embryogenetic stage will enable early judgment on success or failure of embryonic growth.

The third embodiment of the present disclosure has been explained. The third embodiment of the present disclosure is advantageous over the first embodiment and the second embodiment, for its advanced timeliness and low cost for analysis.

5. Fourth Embodiment

Next, the fourth embodiment of the present disclosure will be explained referring to FIG. 18 to FIG. 29. The aforementioned first to third embodiments have mainly dealt with exemplary cases where embryo was used as an example of the biological sample. The biological sample in the present disclosure is, however, not limited to such example. The biological sample in the present disclosure include various samples used for observing vital phenomena from a medical or academic viewpoint.

The biological sample in the present disclosure may be cancer cell, for example. For an exemplary case of cancer cell, characteristic morphological changes in both before and after an event, such as cell division, cell death and so forth can be observed individually. The fourth embodiment of the present disclosure will now detail an exemplary case where a cancer cell is used as the biological sample.

Now the description below will be made referring to the configuration and functions of the information processing device 20A in first embodiment. Detailed description of the configuration and processes of the information processing device 20 will not therefore be made in the embodiment. Alternatively, the fourth embodiment of the present disclosure may be available while combined with the second embodiment or with the third embodiment.

First, occurrence of an event regarding cancer cell will be explained. As described above, characteristic changes in morphology can be observed in cancer cell in events such as cell division, cell death and so forth.

Figure 18:
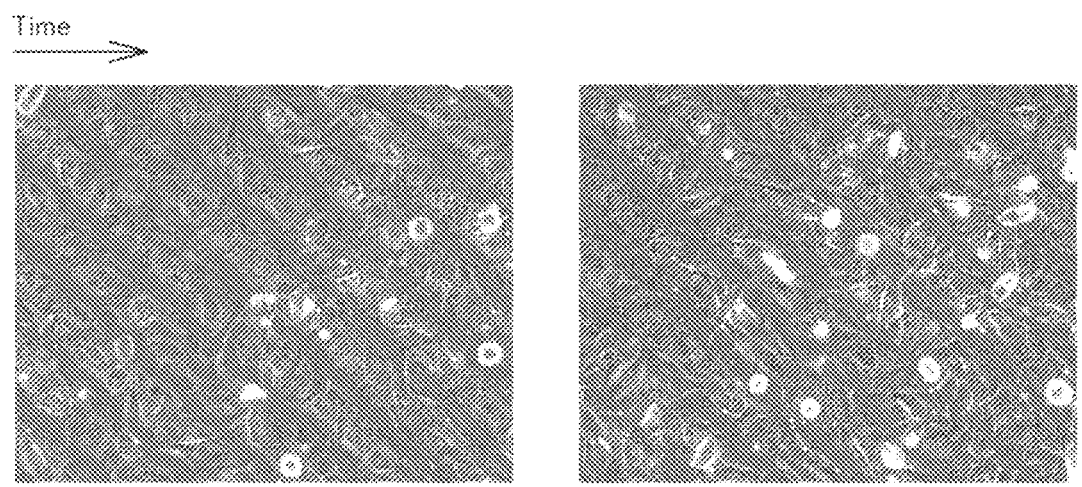
FIG. 18 illustrates exemplary time-lapse images capturing osteoblastoma U2OS cells, according to a third embodiment of the present disclosure.
Figure 19:
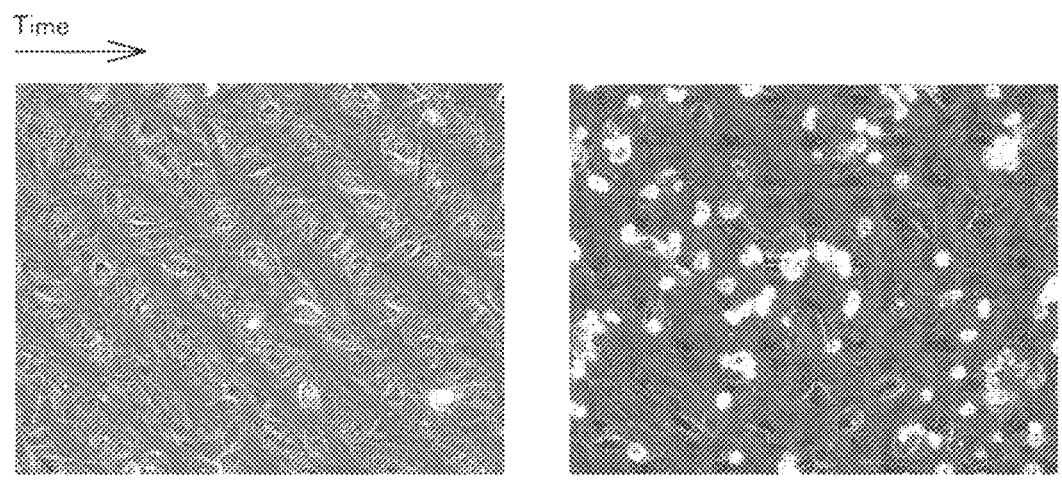
FIG. 19 illustrates exemplary time-lapse images capturing osteoblastoma U2OS cells, according to the embodiment.

First, the morphological changes of cancer cell associated with occurrence of event will be explained referring to FIG. 18 and FIG. 19. FIG. 18 and FIG. 19 are exemplary time-lapse images of osteoblastoma U2OS cells. Left images in FIG. 18 and FIG. 19 are time-lapse images taken immediately after the start of image capturing, and right images are time-lapse images taken 18 hours after the start of image capturing.

Note that FIG. 18 shows the time-lapse images taken without adding a chemical, meanwhile FIG. 19 shows the time-lapse images taken to observe an effect of addition of a chemical having an effect of inducing cell death (apoptosis). The images were captured at 5 fps, 20× magnification, and one hour intervals.

Focusing now on FIG. 18 taken without adding the chemical, it is found from the left and right images that a part of cells are transformed into rounded shape. Such morphological change appears clearly and brightly on the image, since the morphological change of cells modified the phase-contrast image. In this way, the characteristic morphological change can be observed during cell division, prior to occurrence of the event.

On the other hand, focusing now on FIG. 19 taken after adding the chemical that induces cell death, a morphological change of dead cancer cell induced by the chemical can be observed in the right image taken 18 hours after. In a typical course of cell death, the cell contracts, the cytoplasm is vigorously agitated, and the morphological change will no longer be observed several hours after, thereby the cell death may be determined.

On the other hand, in some cases of cell death, the morphological change prior to the cell death would be ambiguous, or visual observation for judging cell death would be time-consuming. Moreover, even cell division often shows a morphological feature similar to cell death. Hence it is often difficult to discriminate cell division and cell death solely from the morphological change in the time-lapse images, possibly causing erroneous discrimination.

According now to the fourth embodiment of the present disclosure, the accuracy of discrimination can be improved by using the time-lapse images in combination with the time-series data of motion size obtained from the kinetic analysis.

Figure 20:
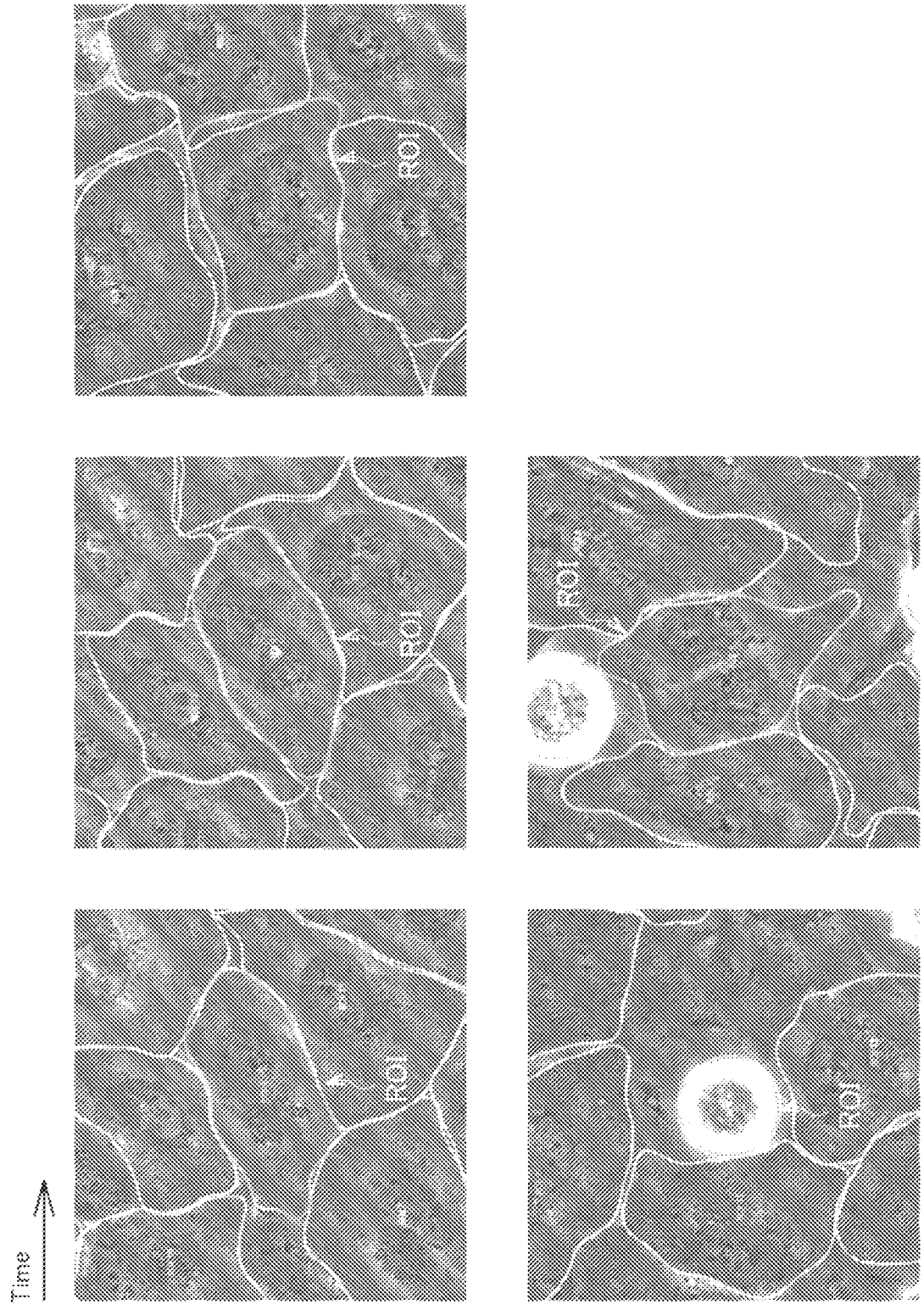
FIG. 20 is a drawing explaining kinetic analysis of cancer cells, according to the embodiment.

FIG. 20 is a drawing explaining kinetic analysis of a cancer cell, according to the embodiment. In the kinetic analysis of the embodiment, temporal changes of motion size were observed in a region of interest that was preset manually or automatically on the basis of morphology or position of the cancer cell. FIG. 20 illustrates temporal changes of the region of interest ROI in the shot video.

Now in FIG. 20, the upper left image is an image shot immediately after the start of video shooting, the upper central image is an image shot one hour after the start of video shooting, and the upper right image is an image shot 10 hours after the start of video shooting. Meanwhile, the lower left image is an image focused on a morphological change observable prior to cell division, and the lower central image is an image showing cell division. Note that the motion size used in the embodiment was obtained by dividing an area in which cytoplasmic streaming was detected (motion area), by an area detected in the region of interest ROI as the cell region (analysis area).

Figure 21:
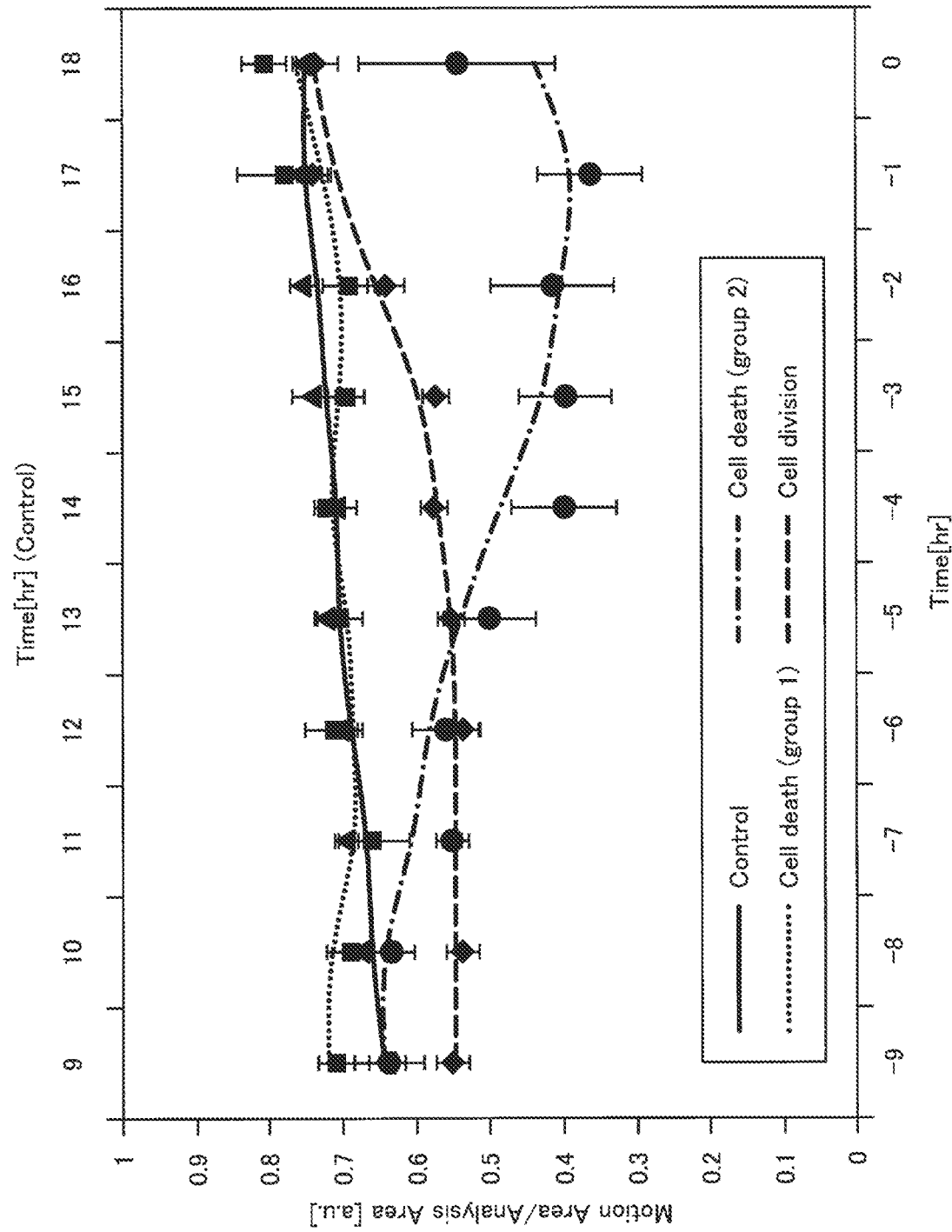
FIG. 21 is a drawing illustrating exemplary results of the kinetic analysis, obtained by the kinetic analysis according to the embodiment.

FIG. 21 is a drawing illustrating exemplary results of kinetic analysis, obtained by the aforementioned analysis. The results of kinetic analysis illustrated in FIG. 21 show temporal changes in averaged motion size and standard error, regarding the cancer cells classified into four groups below, observed over 10 hours prior to the occurrence of event, at one hour intervals (except for control represented by data over 10 hours from the start of video shooting).
(1) Cancer cells resulted in neither division nor death (control)
(2) Cancer cells resulted in cell death (group 1)
(3) Cancer cells resulted in cell death (group 2)
(4) Cancer cells resulted in cell division Note that the classification above was given based on profiles of morphological changes observed on still images. In addition, the dead cancer cells were sub-classified into two groups, namely group 1 and group 2, due to difference in profiles of morphological changes.

Focusing now on the kinetic analysis illustrated in FIG. 21, it is understood that different tendencies of motion size before the event occurs can be observed for the individual groups. For example, the dead cancer cells (group 2) and the cancer cells resulted in cell division showed motion sizes prior to occurrence of event, whose tendencies were largely different.

Figure 22:
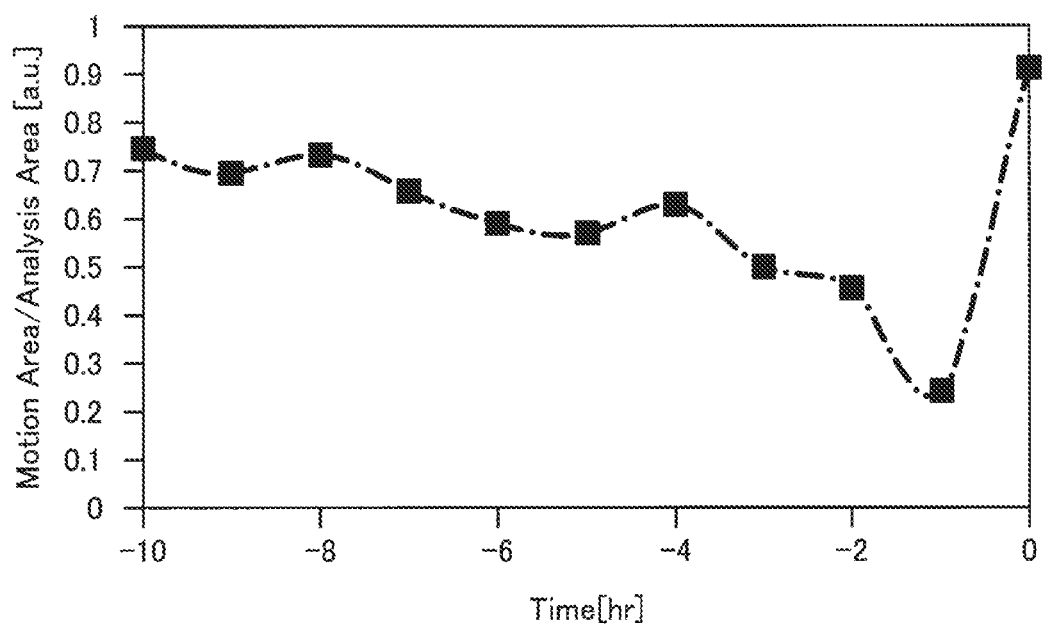
FIG. 22 is a drawing illustrating a result of kinetic analysis of a single dead cancer cell (group 2), according to the embodiment.
Figure 23:
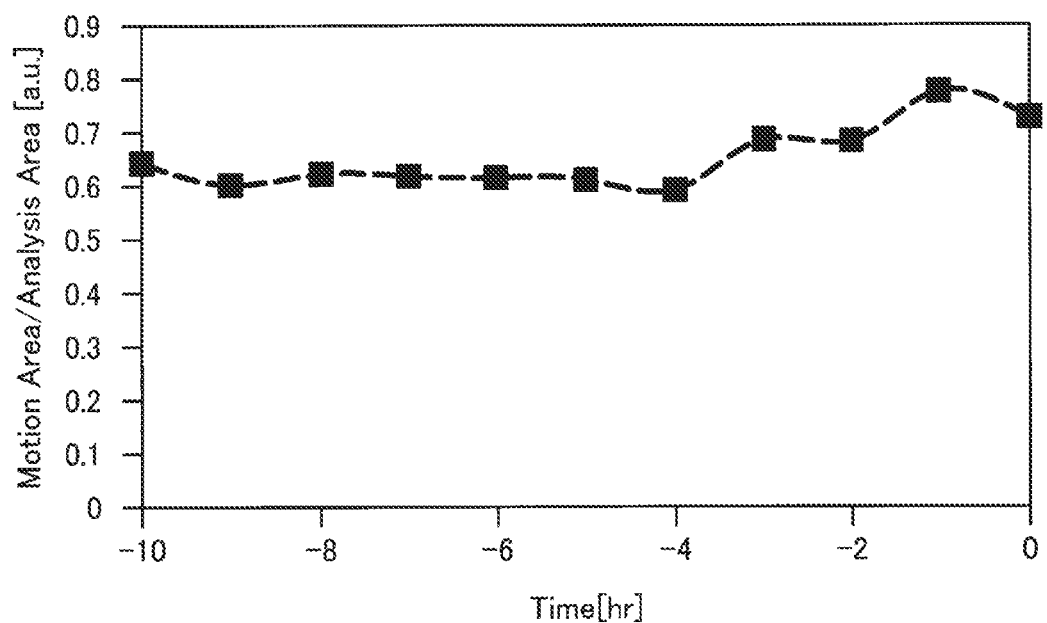
FIG. 23 is a drawing illustrating a result of kinetic analysis of a single divided cell, according to the embodiment.

Referring now to FIG. 22 to FIG. 24, results of kinetic analysis and morphological changes of a single cell will be compared between the dead cancer cell (group 2) and the cancer cells resulted in cell division. FIG. 22 is a drawing illustrating results of kinetic analysis of a single dead cancer cell (group 2). Meanwhile, FIG. 23 is a drawing illustrating results of kinetic analysis of a single cancer cell resulted in cell division. From comparison between FIG. 22 and FIG. 23, it is understood that a distinct difference can be observed between two groups, even when the individual cells were brought into focus. As is clear from above, the results of kinetic analysis can provide an effective benchmark also for discrimination of events regarding cancer cell.

Figure 25:
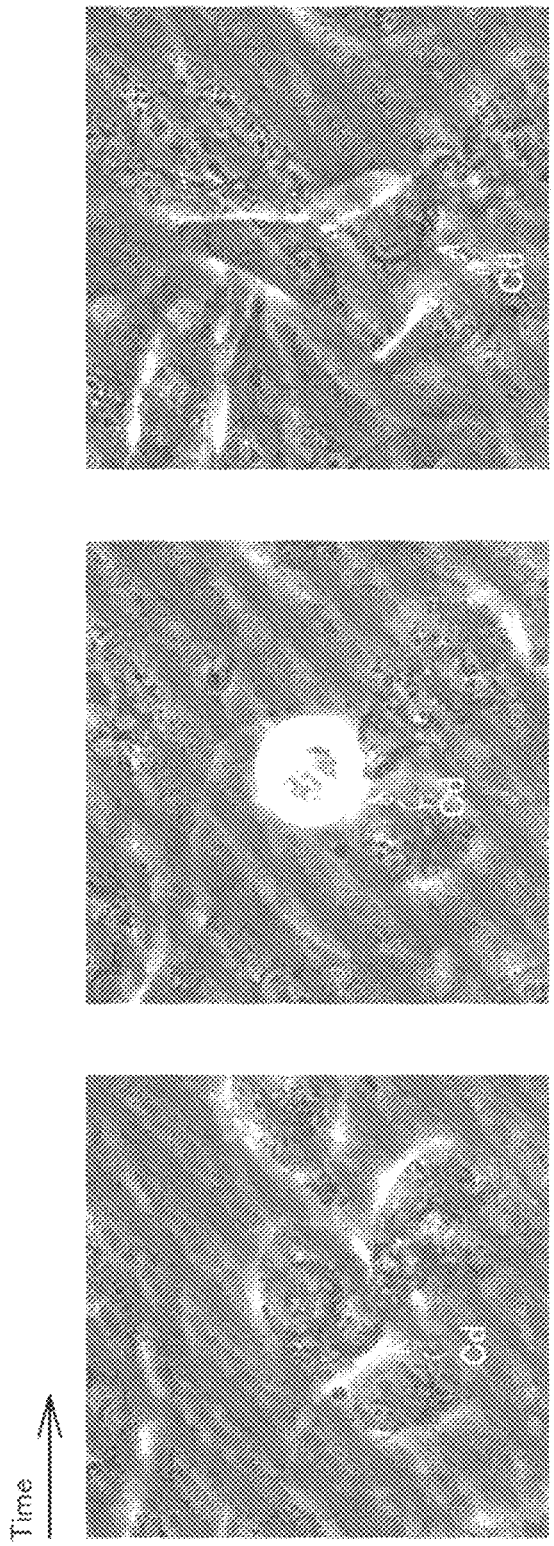
FIG. 25 contains time-lapse images capturing morphological changes in a single divided cancer cell, according to the embodiment.

On the other hand, FIG. 24 contains time-lapse images capturing morphological changes in a single dead cancer cell (group 2) Ca2, and FIG. 25 contains time-lapse images capturing morphological changes in a single cancer cell Cd resulted in cell division. From comparison between FIG. 24 and FIG. 25, it is understood that a similar morphological change can be observed in both groups prior to occurrence of event.

It is therefore difficult to discriminate the aforementioned two groups prior to occurrence of event, solely from the time-lapse images. Moreover, for accurate discrimination, it is necessary to continue observation until the event completely ends.

For this reason, the information processing device 20 of the embodiment may discriminate the event on the basis of both of morphological changes and results of kinetic analysis. According to the information processing device 20 of the embodiment, it now becomes possible to discriminate events regarding cancer cell accurately and within a short time, by using the results of kinetic analysis, even for a case where the discrimination is difficult solely from the morphological changes.

On the other hand, there may be a case where discrimination of event is difficult solely from the results of kinetic analysis, contrary to the cases illustrated in FIG. 22 to FIG. 25. Referring for example to the results of kinetic analysis illustrated in FIG. 21, comparison of the motion size between the cancer cells resulted in neither death nor cell division (Control) with the dead cancer cells (group 1) teaches that there seems to be almost no difference between these two groups.

Figure 26:
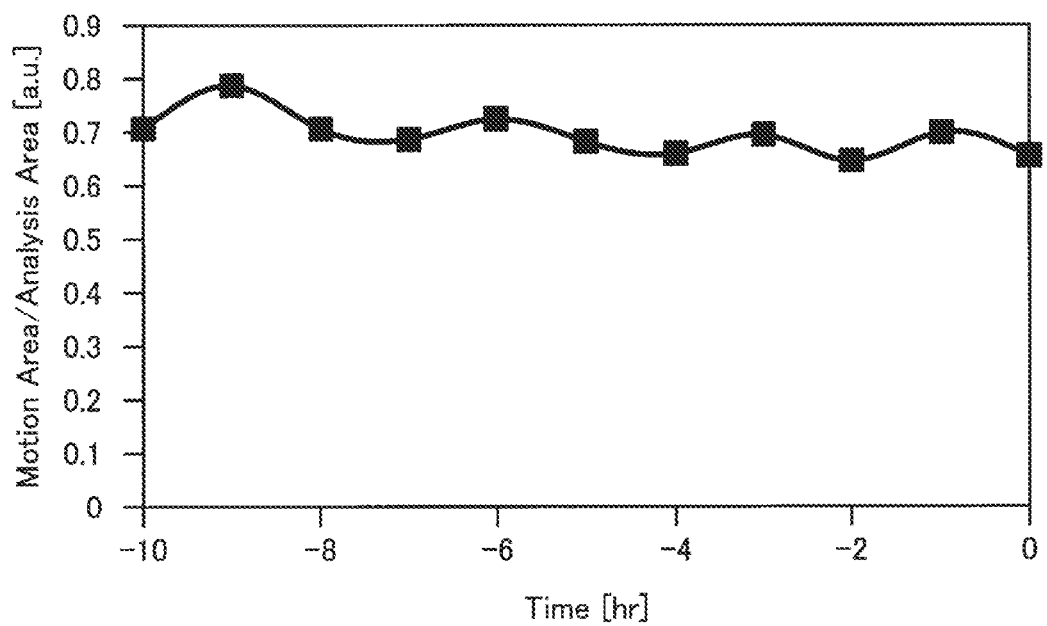
FIG. 26 is a drawing illustrating a result of kinetic analysis of a single cancer cell (Control) resulted in neither death nor division, according to the embodiment.
Figure 27:
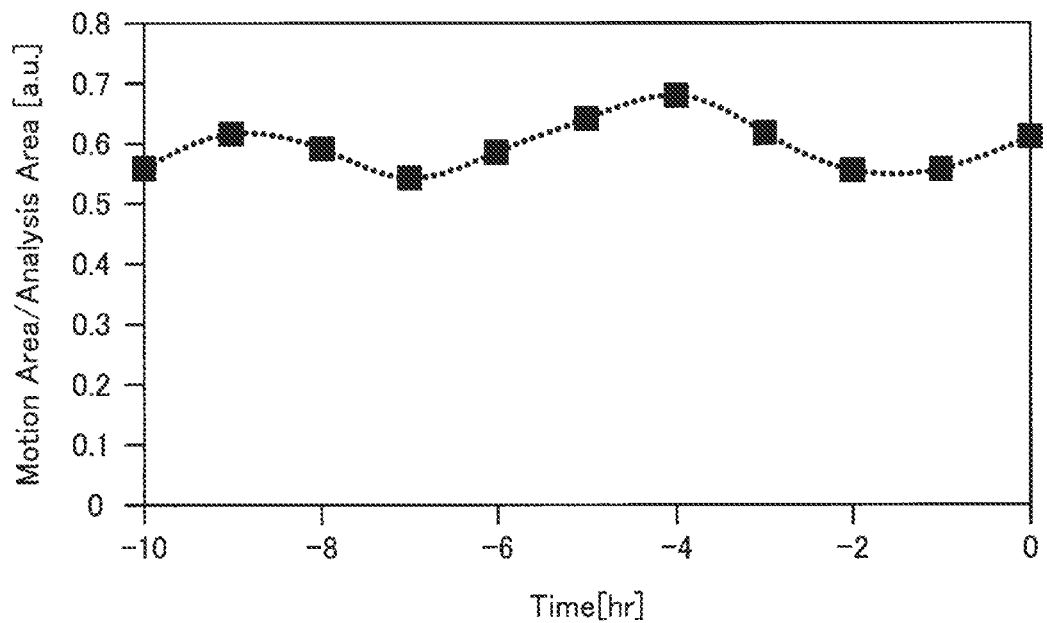
FIG. 27 is a drawing illustrating a result of kinetic analysis of a single dead cancer cell (group 1), according to the embodiment.

Referring now to FIG. 26 to FIG. 29, the cancer cells resulted in neither death nor cell division (Control) and the dead cancer cell (group 1) will be compared with respect to the results of kinetic analysis of a single cell and morphological changes. FIG. 26 is a drawing illustrating a result of kinetic analysis of a single cancer cell (Control) resulted in neither death nor division. Meanwhile, FIG. 27 is a drawing illustrating a result of kinetic analysis of a single dead cancer cell (group 1). Comparing FIG. 26 and FIG. 27, it is understood that no distinct difference between these two groups was observed, even when the individual cells were brought into focus.

Figure 28:
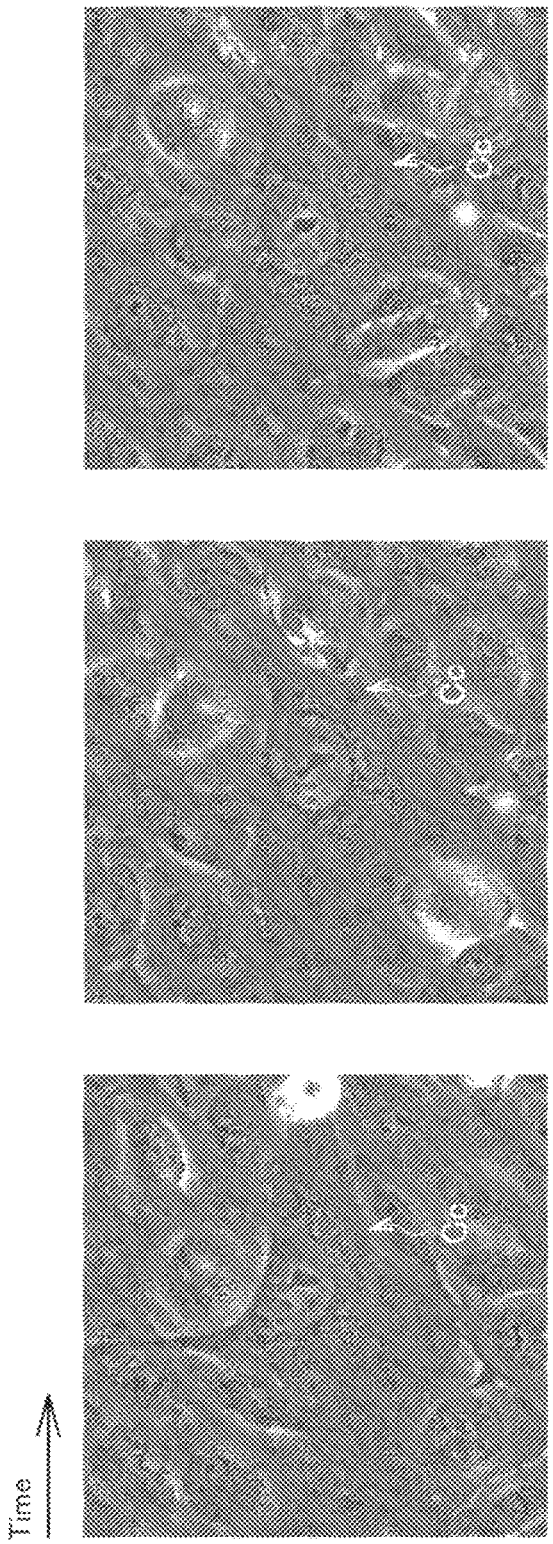
FIG. 28 contains time-lapse images capturing a single cancer cell (Control) neither dead nor divided, according to the embodiment.
Figure 29:
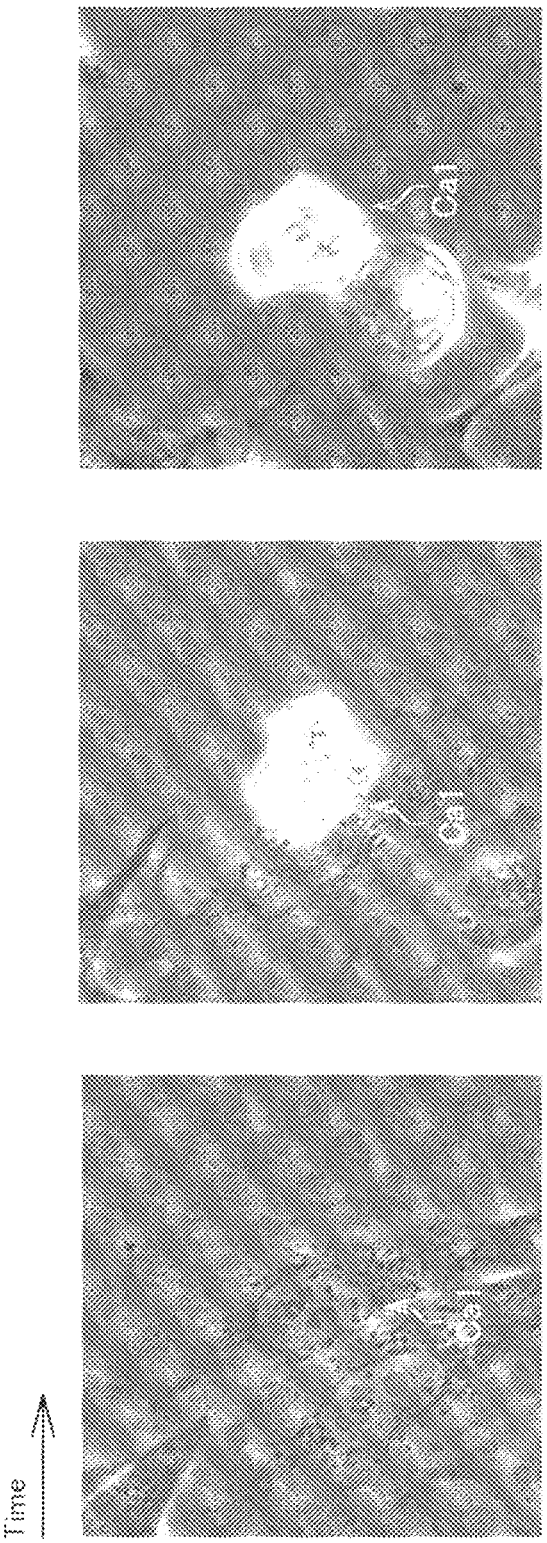
FIG. 29 contains time-lapse images capturing morphological changes in the dead cancer cell (group 1), according to the embodiment.

On the other hand, FIG. 28 contains the time-lapse images capturing a single cancer cell resulted in neither death or cell division (Control), and FIG. 29 contains the time-lapse images capturing morphological changes of dead cancer cell (group 1) Ca1. Comparing FIG. 28 and FIG. 29, it is understood that a characteristic morphological change prior to cell death was observed for the dead cancer cell (group 1)

Ca1, whereas no comparable morphological change was observed for the cancer cell not even resulted in cell division (Control) Cc.

As is clear from above, the observation results of morphological changes may sometimes take advantage over the results of kinetic analysis, depending on types of events to be compared. Nevertheless in such case, the information processing device 20 according to the embodiment is expected to provide event discrimination with higher accuracy than in the case where the discrimination relies solely upon morphological changes, by way of estimation on the basis of both of the results of kinetic analysis and morphological changes.

Moreover, the information processing device 20 according to the embodiment is expected to acquire an event discrimination ability with higher generalization performance, by way of repetitive learning correlating the results of kinetic analysis with the observation results of morphological changes.

For example, the information processing device 20 may be subjected to reinforcement learning in which the information processing device 20 performs discrimination solely relying upon the time-lapse images, and is rewarded with respect to the result of discrimination on the basis of the results of kinetic analysis. With such learning function possessed by the information processing device 20 according to the embodiment, it now also becomes possible to accurately discriminate cell division and cell death, using only the time-lapse images as an input.

Alternatively, the information processing device 20 may be subjected, for example, to supervised learning using result of discrimination on the basis of both of the results of kinetic analysis and observation results of morphological changes, or results of visual discrimination, employed as a teacher.

The information processing device 20 according to the embodiment can accomplish the aforementioned leaning by using neural network that involves deep learning such as CNN (Convolution Neural Network) or RNN (Recurrent Neural Network).

As explained above, the information processing device 20 according to the fourth embodiment of the present disclosure can determine the event regarding cancer cell, by using the first information based on the time-lapse images and the second information based on video. The first information may, for example, be information regarding morphological changes of cancer cell. Meanwhile, the second information may, for example, be information regarding temporal changes in motion size obtained from the results of kinetic analysis of cancer cell.

With such function possessed by the information processing device 20 according to the embodiment, it now becomes possible to discriminate events regarding cancer cell accurately and within a short time. Note that the discrimination of cancer-cell-related events in the fourth embodiment of the present disclosure may be achieved in combination with the individual processes explained in the first to third embodiments, as described previously.

6. Exemplary Hardware Configuration

Figure 30:
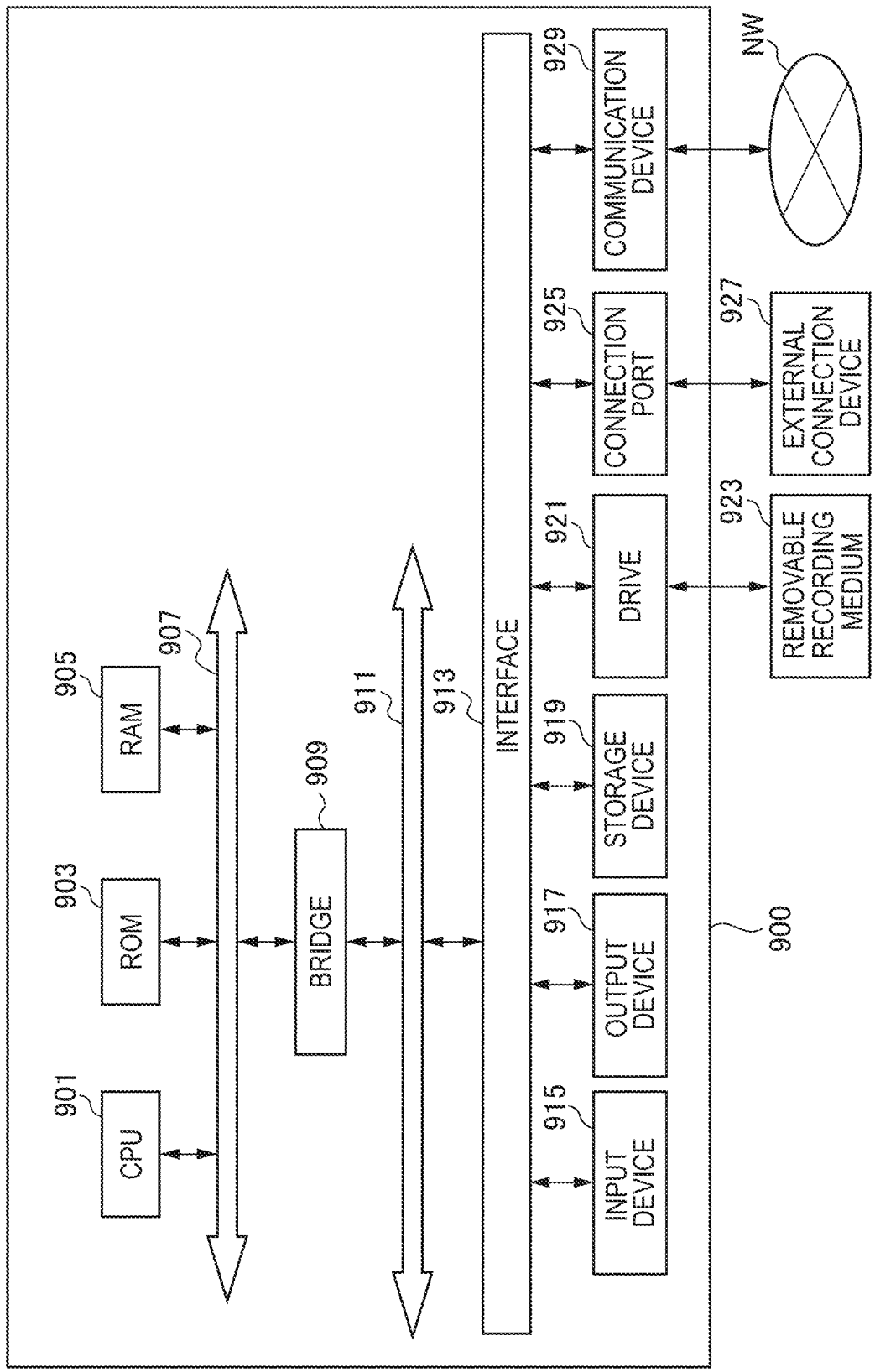
FIG. 30 is a block diagram illustrating an exemplary hardware configuration of an information processing device according to an embodiment of the present disclosure.

Next, with reference to FIG. 30, a hardware configuration of an information processing device according to an embodiment of the present disclosure is described. FIG. 30 is a block diagram illustrating an exemplary hardware configuration of the information processing device according to the embodiment of the present disclosure. An illustrated information processing device 900 can realize the information processing device 20 in the above described embodiment.

The information processing device 900 includes a CPU 901, read only memory (ROM) 903, and random access memory (RAM) 905. In addition, the information processing device 900 may include a host bus 907, a bridge 909, an external bus 911, an interface 913, an input device 915, an output device 917, a storage device 919, a drive 921, a connection port 925, and a communication device 929. The information processing device 900 may include a processing circuit such as a digital signal processor (DSP) or an application-specific integrated circuit (ASIC), instead of or in addition to the CPU 901.

The CPU 901 functions as an arithmetic processing device and a control device, and controls the overall operation or a part of the operation of the information processing device 900 according to various programs recorded in the ROM 903, the RAM 905, the storage device 919, or a removable recording medium 923. For example, the CPU 901 controls overall operations of respective function units included in the information processing device 20 of the above-described embodiment. The ROM 903 stores programs, operation parameters, and the like used by the CPU 901. The RAM 905 transiently stores programs used when the CPU 901 is executed, and parameters that change as appropriate when executing such programs. The CPU 901, the ROM 903, and the RAM 905 are connected with each other via the host bus 907 configured from an internal bus such as a CPU bus or the like. The host bus 907 is connected to the external bus 911 such as a Peripheral Component Interconnect/Interface (PCI) bus via the bridge 909.

The input device 915 is a device operated by a user such as a mouse, a keyboard, a touchscreen, a button, a switch, and a lever. The input device 915 may be a remote control device that uses, for example, infrared radiation and another type of radio waves. Alternatively, the input device 915 may be an external connection device 927 such as a mobile phone that corresponds to an operation of the information processing device 900. The input device 915 includes an input control circuit that generates input signals on the basis of information which is input by a user to output the generated input signals to the CPU 901. The user inputs various types of data and indicates a processing operation to the information processing device 900 by operating the input device 915.

The output device 917 includes a device that can visually or audibly report acquired information to a user. The output device 917 may be, for example, a display device such as an LCD, a PDP, and an OELD, an audio output device such as a speaker and a headphone, and a printer. The output device 917 outputs a result obtained through a process performed by the information processing device 900, in the form of text or video such as an image, or sounds such as audio sounds.

The storage device 919 is a device for data storage that is an exemplary storage unit of the information processing device 900. The storage device 919 includes, for example, a magnetic storage device such as a hard disk drive (HDD), a semiconductor storage device, an optical storage device, or a magneto-optical storage device. The storage device 919 stores therein the programs and various data executed by the CPU 901, and various data acquired from an outside.

The drive 921 is a reader/writer for the removable recording medium 923 such as a magnetic disk, an optical disc, a magneto-optical disk, and a semiconductor memory, and built in or externally attached to the information processing device 900. The drive 921 reads out information recorded on the mounted removable recording medium 923, and outputs the information to the RAM 905. The drive 921 writes the record into the mounted removable recording medium 923.

The connection port 925 is a port used to directly connect devices to the information processing device 900. The connection port 925 may be a Universal Serial Bus (USB) port, an IEEE1394 port, or a Small Computer System Interface (SCSI) port, for example. The connection port 925 may also be an RS-232C port, an optical audio terminal, a High-Definition Multimedia Interface (HDMI (registered trademark)) port, and so on. The connection of the external connection device 927 to the connection port 925 makes it possible to exchange various kinds of data between the information processing device 900 and the external connection device 927.

The communication device 929 is a communication interface including, for example, a communication device for connection to a communication network NW. The communication device 929 may be, for example, a wired or wireless local area network (LAN), Bluetooth (registered trademark), or a communication card for a wireless USB (WUSB). The communication device 929 may also be, for example, a router for optical communication, a router for asymmetric digital subscriber line (ADSL), or a modem for various types of communication. For example, the communication device 929 transmits and receives signals in the Internet or transits signals to and receives signals from another communication device by using a predetermined protocol such as TCP/IP. The communication network NW to which the communication device 929 connects is a network established through wired or wireless connection. The communication network NW is, for example, the Internet, a home LAN, infrared communication, radio wave communication, or satellite communication.

Note that the CPU 901, the ROM 903 and the RAM 905 and so forth can enable the functions of the control unit 200 according to the embodiment. Meanwhile the storage device 919 can enable the function of the storage unit 220 according to the embodiment. Moreover, at least either the connection port 925 or the communication device 929 can enable the function of the communication unit 210 according to the embodiment.

The example of the hardware configuration of the information processing device 900 has been introduced.

7. Conclusion

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

For example, although the information processing system 1 is configured to be provided with the imaging device 10 and information processing device 20 in the above-described embodiment, the present technology is not limited thereto. For example, the imaging device 10 may have the function of the information processing device 20 (For example, kinetic analysis, feature extraction process, various estimation processes, or determination process). In this case, the information processing system 1 is embodied by the imaging device 10. In addition, the information processing device 20 may have the function of the imaging device 10 (imaging function). In this case, the information processing system 1 is embodied by the information processing device 20. Further, the imaging device 10 may have a part of the function of the information processing device 20, and the information processing device 20 may have a part of the function of the imaging device 10.

Note that the information processing system 1 according to the individual embodiments assumed embryo, which is an exemplary biological sample, as a target of application. The embryo as a target of application is not limited to human embryo, but may also be embryo of mammals such as mouse, embryo of non-mammalian animal, or embryo of non-animal multicellular organism. Also note that the information processing system 1 according to one embodiment of the present disclosure is widely applicable not only to embryo, but also to biological samples as a whole, such as cell and biotissue, as described previously.

The steps in the processes performed by the information processing device in the present specification may not necessarily be processed chronologically in the orders described in the flowcharts. For example, the steps in the processes performed by the information processing device may be processed in different orders from the orders described in the flowcharts or may be processed in parallel.

Also, a computer program causing hardware such as the CPU, the ROM, and the RAM included in the information processing device to carry out the equivalent functions as the above-described configuration of the information processing device can be generated. Also, a readable recording medium having the computer program stored therein can be provided.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

An information processing device including:

a first information acquisition section that acquires first information on the basis of a still image in a frame corresponding to a predetermined time point, from among a plurality of images of a biological sample captured in a time-series manner;

a second information acquisition section that acquires second information on the basis of an interframe change of the plurality of images in a predetermined period; and a determination section that determines an event regarding the biological sample, using the first information and the second information.

(2)

The information processing device according to (1), in which the first information contains a first estimation result of a state of the biological sample estimated from a result of image analysis processing of the still image.

(3)

The information processing device according to (2), in which the first estimation result is estimated using a learned model that has learned a preliminarily acquired relation between the event regarding the biological sample and the image of the biological sample.

(4)

The information processing device according to any of (1) to (3), in which the first information contains a feature of the still image, obtained from image analysis processing of the still image.

(5)

The information processing device according to any of (1) to (4), in which the second information acquisition section acquires the second information on the basis of an inter-frame change in a region of interest that is set corresponding to the biological sample.

(6)

The information processing device according to (5), in which the second information contains a kinetic feature obtained on the basis of a result of kinetic analysis regarding the region of interest.

(7)

The information processing device according to (6), in which the second information contains information obtained from the kinetic feature that is specified on the basis of a temporal change of the kinetic feature.

(8)

The information processing device according to (6) or (7), in which the second information contains information obtained from the kinetic feature that falls in a time window defined in reference to the predetermined time point.

(9)

The information processing device according to (7) or (8), in which the information obtained from the kinetic feature is a waveform of the kinetic feature, and the second information contains an analytical result of the waveform of the kinetic feature.

(10)

The information processing device according to any of (6) to (9), in which the kinetic feature contains a feature based on a morphological change in the region of interest.

(11)

The information processing device according to any of (6) to (10), in which the kinetic feature contains a feature based on motion in the region of interest.

(12)

The information processing device according to any of (6) to (11), in which the kinetic feature contains a feature based on pixel information of the image.

(13)

The information processing device according to any of (6) to (12), in which the second information contains a second estimation result of a state of the biological sample, estimated from the kinetic feature.

(14)

The information processing device according to (13), in which the second estimation result is estimated using a learned model that has learned a preliminarily acquired relation between the event regarding the biological sample and the kinetic feature of the biological sample.

(15)

The information processing device according to (13) or (14), in which, in a case where the first estimation result of a state of the biological sample estimated from a result of image analysis processing of the still image, and a second estimation result of a state of the biological sample estimated from the kinetic feature are used for estimation, the determination section determines the event regarding the biological sample, on the basis of likelihood obtained by collating the first estimation result with the second estimation result.

(16)

The information processing device according to any of (1) to (15), in which the determination section determines the event regarding the biological sample, on the basis of combination of the first information and the second information.

(17)

The information processing device according to any of (1) to (16), in which the plurality of images contains images continuously captured within the predetermined period with the predetermined time point defined as a start time of image capturing.

(18)

An information processing method including, by a processor:

acquiring first information on the basis of a still image in a frame corresponding to a predetermined time point, from among a plurality of images of a biological sample captured in a time-series manner;

acquiring second information on the basis of an inter-frame change of the plurality of images in a predetermined period; and determining an event regarding the biological sample, using the first information and the second information.

(19)

An information processing system including:

an imaging device including an imaging unit that produces an image by image capturing; and an information processing device including a first information acquisition section that acquires first information on the basis of a still image in a frame corresponding to a predetermined time point, from among a plurality of images of a biological sample captured by the imaging unit in a time-series manner, a second information acquisition section that acquires second information on the basis of an inter-frame change of the plurality of images in a predetermined period, and a determination section that determines an event regarding the biological sample, using the first information and the second information.

REFERENCE SIGNS LIST 1 information processing system
10 imaging device
20 information processing device
101 imaging section
102 imaging control section
200 control unit
201 image acquisition section
202 first estimation section
203 kinetic analysis section
204 feature extraction section
205 second estimation section
206 determination section
207 output control section
210 communication unit
220 storage unit
251 image feature acquisition section

The invention claimed is:

1. An information processing device, comprising:
a central processing unit (CPU) configured to:
acquire first information based on an image from a plurality of images of a biological sample captured in a time-series manner,
wherein the image is in a frame corresponding to a specific time point;

set a region of interest corresponding to the biological sample;

obtain a kinetic feature based on a result of kinetic analysis of the region of interest;

obtain a waveform of the kinetic feature, wherein the waveform is based on a temporal change of the kinetic feature;

acquire second information based on an interframe change in the region of interest of the plurality of images in a specific period, wherein the second information includes an analytical result of the waveform of the kinetic feature; and determine an event of the biological sample based on the first information and the second information.

2. The information processing device according to claim 1, wherein the CPU is further configured to:

execute an image analysis processing operation of the image; and estimate a state of the biological sample as a first estimation result, based on a result of the image analysis processing operation, and the first information contains the first estimation result.

3. The information processing device according to claim 2, wherein the estimation of the first estimation result is based on a learned model that has learned a preliminarily acquired relation between the event of the biological sample and the image of the biological sample.

4. The information processing device according to claim 1, wherein the CPU is further configured to execute an image analysis processing operation of the image, and the first information contains a feature of the image, obtained from the image analysis processing operation.

5. The information processing device according to claim 1, wherein the second information contains third information obtained from the kinetic feature that falls in a time window defined in reference to the specific time point.

6. The information processing device according to claim 1, wherein the kinetic feature contains a feature based on a morphological change in the region of interest.

7. The information processing device according to claim 1, wherein the kinetic feature contains a feature based on motion in the region of interest.

8. The information processing device according to claim 1, wherein the kinetic feature contains a feature based on pixel information of the image.

9. The information processing device according to claim 1, wherein the CPU is further configured to estimate a state of the biological sample as a first estimation result based on the kinetic feature, and the second information contains the first estimation result.

10. The information processing device according to claim 9, wherein an estimation of a second estimation result is based on a learned model that has learned a preliminarily acquired relation between the event of the biological sample and the kinetic feature of the biological sample.

11. The information processing device according to claim 9, wherein the CPU is further configured to:

execute an image analysis processing operation of the image;

estimate the state of the biological sample as a second estimation result, based on a result of the image analysis processing operation;

collate the first estimation result with the second estimation result; and determine, in a case where the first estimation result, and the second estimation result are used for the estimation the state of the biological sample, the event of the biological sample based on a likelihood obtained by the collation of the first estimation result with the second estimation result.

12. The information processing device according to claim 1, wherein the CPU is further configured to determine the event of the biological sample based on a combination of the first information and the second information.

13. The information processing device according to claim 1, wherein the plurality of images is continuously captured within the specific period with the specific time point defined as a start time of an image capturing operation.

14. An information processing method comprising:

acquiring, by a processor, first information based on an image from a plurality of images of a biological sample captured in a time-series manner, wherein the image is in a frame corresponding to a specific time point;

setting, by the processor, a region of interest corresponding to the biological sample;

obtaining, by the processor, a kinetic feature based on a result of kinetic analysis of the region of interest;

obtaining, by the processor, a waveform of the kinetic feature, wherein the waveform is based on a temporal change of the kinetic feature;

acquiring, by the processor, second information based on an interframe change in the region of interest of the plurality of images in a specific period, wherein the second information includes an analytical result of the waveform of the kinetic feature; and determining, by the processor, an event of the biological sample based on the first information and the second information.

15. An information processing system, comprising:

an imaging device including an imaging unit configured to output an image; and an information processing device including:

a central processing unit (CPU) configured to:

acquire first information based on the image from a plurality of images of a biological sample captured by the imaging unit in a time-series manner, wherein the image is in a frame corresponding to a specific time point;

set a region of interest corresponding to the biological sample;

obtain a kinetic feature based on a result of kinetic analysis of the region of interest;

obtain a waveform of the kinetic feature, wherein the waveform is based on a temporal change of the kinetic feature;

acquire second information based on an interframe change in the region of interest of the plurality of images in a specific period, wherein the second information includes an analytical result of the waveform of the kinetic feature; and determine an event of the biological sample based on the first information and the second information.

* * * * *